(12) United States Patent
Brink et al.

(10) Patent No.: US 12,194,301 B2
(45) Date of Patent: *Jan. 14, 2025

(54) MANAGING THERAPY DELIVERY BASED ON PHYSIOLOGICAL MARKERS

(71) Applicant: Medtronic, Inc., Minneapolis, MN (US)

(72) Inventors: Thaddeus S. Brink, St. Paul, MN (US); Dwight E. Nelson, Shoreview, MN (US); Xin Su, Plymouth, MN (US); Lance Zirpel, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 457 days.

This patent is subject to a terminal disclaimer.

(21) Appl. No.: 17/552,813

(22) Filed: Dec. 16, 2021

(65) Prior Publication Data

US 2022/0105348 A1     Apr. 7, 2022

Related U.S. Application Data

(63) Continuation of application No. 16/663,023, filed on Oct. 24, 2019, now Pat. No. 11,376,438, which is a
(Continued)

(51) Int. Cl.
*A61N 1/36* (2006.01)
*A61B 5/00* (2006.01)
(Continued)

(52) U.S. Cl.
CPC .......... *A61N 1/36139* (2013.01); *A61B 5/204* (2013.01); *A61B 5/4836* (2013.01);
(Continued)

(58) Field of Classification Search
CPC ............ A61N 1/36139; A61N 1/36007; A61B 5/4836; A61B 5/204; A61B 5/1113;
(Continued)

(56) References Cited

U.S. PATENT DOCUMENTS

| 5,258,745 A | 11/1993 | Colling |
| 6,266,557 B1 | 7/2001 | Roe et al. |

(Continued)

FOREIGN PATENT DOCUMENTS

| WO | 2004047914 A1 | 6/2004 |
| WO | 2008130467 A1 | 10/2008 |

OTHER PUBLICATIONS

Prosecution History from U.S. Appl. No. 15/256,242, now issued U.S. Pat. No. 10,456,580, dated Jan. 9, 2016 through Jan. 9, 2019, 68 pp.
(Continued)

*Primary Examiner* — Rex R Holmes
(74) *Attorney, Agent, or Firm* — Shumaker & Sieffert, P.A.

(57) ABSTRACT

Devices, systems, and methods may manage therapy delivery to a patient based on one or more physiological markers. In some examples, a method includes detecting a physiological marker that occurs prior in time to a dysfunctional phase of a physiological cycle, wherein a dysfunctional state of the physiological cycle occurs during the dysfunctional phase without treatment, responsive to detecting the physiological marker, initiating a first phase of the physiological cycle having a duration of time. The method may also include, responsive to the first phase elapsing, controlling a therapy delivery module to deliver neurostimulation therapy during a second phase that begins prior to the dysfunctional phase, wherein the neurostimulation therapy is configured to treat the dysfunctional state.

24 Claims, 13 Drawing Sheets

Related U.S. Application Data continuation of application No. 15/256,242, filed on Sep. 2, 2016, now Pat. No. 10,456,580.

(60) Provisional application No. 62/214,750, filed on Sep. 4, 2015.

(51) Int. Cl.
*A61B 5/20* (2006.01)
*A61B 5/0538* (2021.01)
*A61B 5/11* (2006.01)
*A61B 5/391* (2021.01)

(52) U.S. Cl.
CPC ........ *A61N 1/36007* (2013.01); *A61B 5/0538* (2013.01); *A61B 5/1113* (2013.01); *A61B 5/1116* (2013.01); *A61B 5/207* (2013.01); *A61B 5/391* (2021.01)

(58) Field of Classification Search
CPC ... A61B 5/04882; A61B 5/207; A61B 5/0538; A61B 5/1116
See application file for complete search history.

(56) References Cited

U.S. PATENT DOCUMENTS

| | | | |
|---|---|---|---|
| 6,652,449 | B1 | 11/2003 | Gross et al. |
| 6,725,094 | B2 | 4/2004 | Saberski |
| 7,147,606 | B1 | 12/2006 | Chang et al. |
| 7,415,308 | B2 | 8/2008 | Gerber et al. |
| 7,515,965 | B2 | 4/2009 | Gerber et al. |
| 8,374,696 | B2 | 2/2013 | Sanchez et al. |
| 8,439,845 | B2 | 5/2013 | Folkerts et al. |
| 8,825,169 | B2 | 9/2014 | Zhu et al. |
| 8,831,735 | B2 | 9/2014 | John |
| 9,168,374 | B2 | 10/2015 | Su |
| 10,456,580 | B2 * | 10/2019 | Brink ............... A61B 5/204 |
| 11,376,438 | B2 * | 7/2022 | Brink ............... A61N 1/36139 |
| 2006/0190051 | A1 | 8/2006 | Gerber et al. |
| 2007/0255176 | A1 | 11/2007 | Rondoni et al. |
| 2008/0052030 | A1 | 2/2008 | Olson et al. |
| 2010/0234696 | A1 | 9/2010 | Li et al. |
| 2011/0264163 | A1 | 10/2011 | Tracey et al. |
| 2012/0197338 | A1 | 8/2012 | Su et al. |
| 2013/0079840 | A1 | 3/2013 | Su et al. |
| 2013/0079841 | A1 | 3/2013 | Su et al. |
| 2013/0289659 | A1 | 10/2013 | Nelson et al. |
| 2013/0303942 | A1 | 11/2013 | Damaser et al. |
| 2014/0277250 | A1 | 9/2014 | Su et al. |
| 2015/0328454 | A1 | 11/2015 | Lambert |
| 2016/0243358 | A1 | 8/2016 | Creasey et al. |
| 2016/0354028 | A1 | 12/2016 | Damaser et al. |
| 2017/0065821 | A1 | 3/2017 | Brink et al. |
| 2017/0239470 | A1 | 8/2017 | Wei et al. |
| 2020/0054878 | A1 | 2/2020 | Brink et al. |
| 2020/0230406 | A1 | 7/2020 | Brink et al. |

OTHER PUBLICATIONS

Prosecution History from U.S. Appl. No. 16/663,023, dated Nov. 13, 2019 through Dec. 27, 2021, 40 pp.

Stanslaski et al., "A Chronically-Implantable Neural Coprocessor for Investigating the Treatment of Neurological Disorders." IEEE Transactions on Biomedical Circuits and Systems, vol. 12, No. 6, Dec. 2018, 15 pp.

Bastiaanssen et al., "Learning Procedure in a Neural Control Model for the Urinary Bladder," Neurourology and Urodynamics, vol. 12, No. 3, DOI: 10.1002/nau.1930120314, (Applicant points out, in accordance with MPEP 609.04 (a), that the year of publication, 1993, is sufficiently earlier than the effective U.S. filing date, so that the particular month of publication is not in issue.), 1993, pp. 285-288.

Dunne et al., "Supervised Learning Classifiers for Electrical Impedance-based Bladder State Detection," Scientific Reports, vol. 8, No. 5363, DOI:10.1038/s41598-018-23786-5, Mar. 2018, 12 pp.

Geramipour et al., "Neural Network Based Forward Prediction of Bladder Pressure Using Pudendal Nerve Electrical Activity," 2015 37th Annual International Conference of the IEEE Engineering in Medicine and Biology Society (EMBC), IEEE, DOI: 10.1109/EMBC.2015.7319454, Aug. 2015, 4 pp.

Jabbari et al., "Estimation of Bladder Pressure and Volume from the Neural Activity of Lumbosacral Dorsal Horn Using a Long-Short-Term-Memory-based Deep Neural Network," Scientific Reports, vol. 9, No. 18128, DOI: 10.1038/s41598-019-54144-8, Dec. 2019, 15 pp.

Navya et al., "Application of Signal Processing in the Detection of Urinary Dysfunction: A Review on Different Techniques," 2020 International Conference on Power, Instrumentation, Control and Computing (PICC), IEEE, DOI: 10.1109/PICC51425.2020.9362378, Dec. 2020, 6 pp.

Notice of Allowance from U.S. Appl. No. 16/663,023, dated Mar. 8, 2022, 8 pp.

Stanslaski et al., "A Chronically-Implantable Neural Coprocessor for Investigating the Treatment of Neurological Disorders," IEEE, Nov. 7, 2018, 15 pp.

* cited by examiner

MANAGING THERAPY DELIVERY BASED ON PHYSIOLOGICAL MARKERS

This application is a continuation of U.S. patent application Ser. No. 16/663,023, filed on Oct. 24, 2019 and issued as U.S. Pat. No. 11,376,438 on Jul. 5, 2022, which is a continuation of U.S. patent application Ser. No. 15/256,242, filed on Sep. 2, 2016 and issued as U.S. Pat. No. 10,456,580 on Oct. 29, 2019, which claims the benefit of U.S. Provisional Patent Application No. 62/214,750, filed on Sep. 4, 2015, the entire contents of these applications are incorporated herein by reference.

TECHNICAL FIELD

The disclosure relates to medical devices and, more particularly, medical devices that deliver therapy to a patient.

BACKGROUND

Disease, age, and injury can impair physiological functions of a patient. In some situations, the physiological functions are completely impaired. In other examples, the physiological function may operate sufficiently at some times or under some conditions and operate inadequately at other times or at other conditions. In one example, bladder dysfunction, such as overactive bladder, urgency, or urinary incontinence, is a problem that may afflict people of all ages, genders, and races. Various muscles, nerves, organs and conduits within the pelvic floor cooperate to collect, store and release urine. A variety of disorders may compromise urinary tract performance, and contribute to an overactive bladder, urgency, or urinary incontinence that interferes with normal physiological function. Many of the disorders may be associated with aging, injury or illness.

Urinary incontinence may include urge incontinence and stress incontinence. In some examples, urge incontinence may be caused by disorders of peripheral or central nervous systems that control bladder micturition reflexes. Some patients may also suffer from nerve disorders that prevent proper triggering and operation of the bladder, sphincter muscles or nerve disorders that lead to overactive bladder activities or urge incontinence. In some cases, urinary incontinence can be attributed to improper sphincter function, either in the internal urinary sphincter or external urinary sphincter.

SUMMARY

In general, the disclosure is directed to devices, systems, and techniques for managing therapy delivery based on physiological markers. A system may control delivery of neurostimulation therapy to a patient based on one or more detectable physiological markers and time delivery relative to these physiological markers. Accordingly, the system may time delivery of a targeted neurostimulation therapy to a particular period after detecting the one or more physiological markers. In some examples, the system may withhold neurostimulation therapy delivery to a patient during certain times or phases of a physiological cycle until the system determines that neurostimulation should be delivered. Alternatively, the system may deliver different neurostimulation during the period of time between the detected physiological marker and when the targeted neurostimulation is to be delivered later in the physiological cycle, e.g., the system may modify or change one or more parameters defining the neurostimulation at a time after the physiological marker is detected. In this manner, the system may control delivery of neurostimulation in response to detecting a physiological marker or during a phase later in time from the physiological marker.

For example, the system may monitor a bladder fill cycle for a patient and control the time of delivery of neurostimulation to occur during a particular phase of the fill cycle. After a voiding event (e.g., a type of physiological marker) is detected, the system may withhold neurostimulation during a first phase of the fill cycle and begin delivery of neurostimulation for a later second phase of the fill cycle where neurostimulation may be more effective at reducing or eliminating a dysfunctional state of the bladder such as urinary incontinence. In this manner, the system may predict the phase of the fill cycle during which neurostimulation should be delivered and deliver neurostimulation during this phase.

In one example, the disclosure is directed to a method that includes monitoring, by one or more processors, a fill cycle of a bladder of a patient, the fill cycle starting after completion of a first voiding event and ending at the completion of a second voiding event, determining, by the one or more processors and based on one or more physiological markers associated with the fill cycle, a first phase including and following the start of the fill cycle and a second phase of the fill cycle immediately following the first phase, wherein the second phase is determined to include delivery of neurostimulation therapy configured to inhibit contraction of a bladder of the patient, and controlling, by the one or more processors, a medical device to deliver the neurostimulation therapy to the patient during the second phase of the fill cycle.

In another example, the disclosure is directed to a system that includes one or more processors configured to monitor a fill cycle of a bladder of a patient, the fill cycle starting after completion of a first voiding event and ending at the completion of a second voiding event, determine, based on one or more physiological markers associated with the fill cycle, a first phase including and following the start of the fill cycle and a second phase of the fill cycle immediately following the first phase, wherein the second phase is determined to include delivery of neurostimulation therapy configured to inhibit contraction of a bladder of the patient, and control a medical device to deliver the neurostimulation therapy to the patient during the second phase of the fill cycle.

In a further aspect, the disclosure is directed to a non-transitory computer-readable medium including instructions that, when executed, cause one or more processors to monitor a fill cycle of a bladder of a patient, the fill cycle starting after completion of a first voiding event and ending at the completion of a second voiding event, determine, based on one or more physiological markers associated with the fill cycle, a first phase including and following the start of the fill cycle and a second phase of the fill cycle immediately following the first phase, wherein the second phase is determined to include delivery of neurostimulation therapy configured to inhibit contraction of a bladder of the patient, and control a medical device to deliver the neurostimulation therapy to the patient during the second phase of the fill cycle In another aspect, the disclosure is directed to a system comprising means for monitoring a fill cycle of a bladder of a patient, the fill cycle starting after completion of a first voiding event and ending at the completion of a second voiding event, means for determining, based on one or more physiological markers associated with the fill cycle, a first phase including and following the start of the fill cycle and a second phase of the fill cycle immediately following the first phase, wherein the second phase is determined to include delivery of neurostimulation therapy configured to inhibit contraction of a bladder of the patient, and means for controlling a medical device to deliver the neurostimulation therapy to the patient during the second phase of the fill cycle.

In another aspect, the disclosure is directed to a method that includes detecting, by one or more processors, a physiological marker that occurs prior in time to a dysfunctional phase of a physiological cycle, wherein a dysfunctional state of the physiological cycle occurs during the dysfunctional phase without treatment, responsive to detecting the physiological marker, initiating, by the one or more processors, a first phase of the physiological cycle having a duration of time, withholding, by the one or more processors, delivery of neurostimulation therapy for the duration of time of the first phase, and responsive to the first phase elapsing, controlling, by the one or more processors, a therapy delivery module to deliver neurostimulation therapy during a second phase that begins prior to the dysfunctional phase, wherein the neurostimulation therapy is configured to treat the dysfunctional state The details of one or more examples are set forth in the accompanying drawings and the description below. Other features, objects, and advantages of the disclosure will be apparent from the description and drawings, and from the claims.

DETAILED DESCRIPTION

Figure 1:
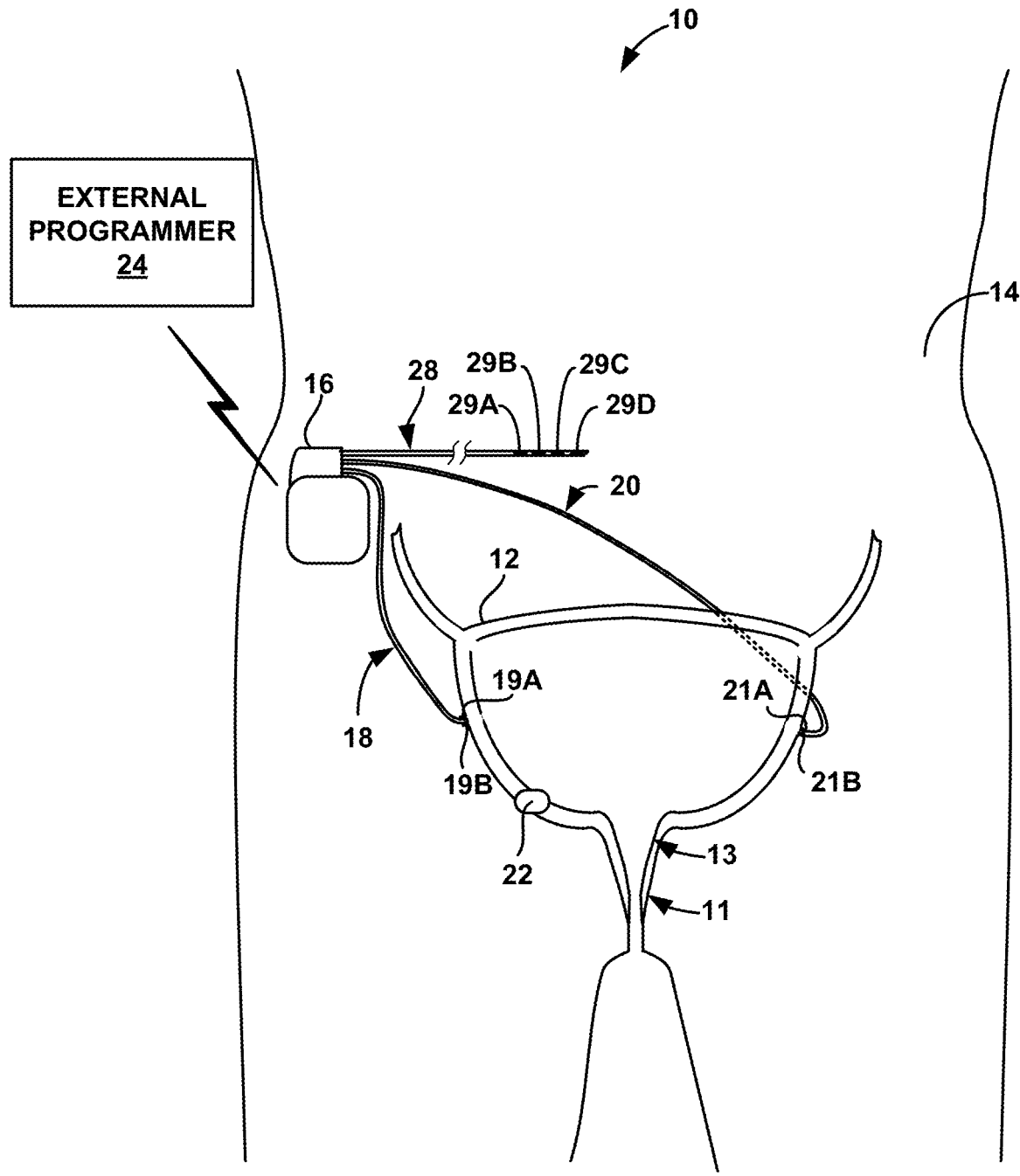
FIG. 1 is a conceptual diagram illustrating an example system that manages delivery of neurostimulation to a patient to manage bladder dysfunction, such as overactive bladder, urgency, or urinary incontinence.

The disclosure is directed to devices, systems, and techniques for managing the delivery of electrical stimulation to a patient such that selective delivery of neurostimulation based on one or more physiological markers may reduce or eliminate a dysfunctional state. The techniques may be used to provide therapy for a variety of dysfunctions, diseases or disorders. For purposes of illustration, but without limitation, use of the techniques will be described below with respect to bladder dysfunction. Bladder dysfunction generally refers to a condition of improper functioning of the bladder or urinary tract, and may include, for example, an overactive bladder, urgency, or urinary incontinence. Overactive bladder (OAB) is a patient condition that may include symptoms, such as urgency, with or without urinary incontinence. Urgency is a sudden, compelling urge to urinate, and may often, though not always, be associated with urinary incontinence. Urinary incontinence refers to a condition of involuntary loss of urine, and may include urge incontinence, stress incontinence, or both stress and urge incontinence, which may be referred to as mixed urinary incontinence. As used in this disclosure, the term "urinary incontinence" includes disorders in which urination occurs when not desired, such as stress or urge incontinence. Other bladder dysfunctions may include disorders such as non-obstructive urinary retention.

One type of therapy for treating bladder dysfunction includes delivery of continuous electrical stimulation to a target tissue site within a patient to cause a therapeutic effect during delivery of the electrical stimulation. For example, delivery of electrical stimulation from an implantable medical device (IMD) to a target therapy site, e.g., a tissue site that delivers stimulation to modulate activity of a spinal nerve (e.g., a sacral nerve), a pudendal nerve, dorsal genital nerve, a tibial nerve, an inferior rectal nerve, a perineal nerve, or branches of any of the aforementioned nerves, may provide an immediate therapeutic effect for bladder dysfunction, such as a desired reduction in frequency of bladder contractions. In some cases, electrical stimulation of the sacral nerve may modulate afferent nerve activities to restore urinary function during the electrical stimulation. However, continuous electrical stimulation or other types of neurostimulation (e.g., drug delivery therapy) may provide neurostimulation during unnecessary phases of a physiological cycle that may cause undesirable side effects, accommodation, less focused therapy, and increased energy usage by the medical device delivering therapy.

In contrast to this type of continuous neurostimulation therapy, devices, systems, and techniques described in this disclosure are directed to managing delivery of neurostimulation therapy based on timing with one or more physiological marker such that neurostimulation is delivered and withheld based on the one or more physiological markers. For example, the physiological markers may be indicative of one or more points within a physiological cycle. The system may monitor the patient for occurrence of the physiological marker or markers as a trigger to stop delivery of neurostimulation therapy, start neurostimulation therapy, or time the delivery of neurostimulation to begin at a later point within the physiological cycle.

Timing the delivery may involve predicting the appropriate phase within the physiological cycle for delivery of neurostimulation based on one or more prior physiological cycles. For example, the system may deliver neurostimulation during a phase that begins prior to, and may also terminate prior to, a dysfunctional phase during which a dysfunctional state typically occurs during the physiological cycle. In this manner, the system may effectively reduce or eliminate the dysfunctional phase by preemptively delivering neurostimulation and withholding neurostimulation during one or more phases of the physiological cycle at which neurostimulation is unnecessary or even detrimental to treating the dysfunctional state. By delivering and withholding neurostimulation based on one or more physiological markers, the system may reduce undesirable side effects from neurostimulation delivered during phases of the cycle that do not benefit from neurostimulation and/or extended periods of neurostimulation delivery, increase efficacy of the neurostimulation therapy, increase durability of the therapy, decrease tissue accommodation to the therapy, decrease energy usage (e.g., during electrical stimulation therapy), and/or decrease material usage (e.g., drug delivery therapy).

In one example, a system may monitor a bladder fill cycle (e.g., a type of physiological cycle) for a patient and time delivery of neurostimulation to occur during a particular phase (e.g., one of a plurality of phases) of the fill cycle. After a voiding event (e.g., a type of physiological marker) is detected, the system may withhold neurostimulation during a first phase of the fill cycle and begin delivery of neurostimulation for a later second phase of the fill cycle where neurostimulation may be more effective at reducing or eliminating a dysfunctional state of the bladder such as urinary incontinence. In this manner, the system may predict the phase of the fill cycle during which neurostimulation should be delivered and deliver neurostimulation during this phase. In some examples, the system may time the beginning of the neurostimulation delivery phase from the detected void event (e.g., the beginning or end of the void event) and estimate the time during the following fill cycle to re-deliver the neurostimulation therapy. The system may predict this time for neurostimulation based on prior fill cycles of the patient and to occur prior to bladder contraction dysfunction (e.g., a dysfunctional state) that may case urinary incontinence.

As will be discussed further below, it has been observed in animal studies that neurostimulation delivered at certain times during the bladder full cycle are responsible for increased bladder capacity, and urine retention. Therefore, a system can withhold neurostimulation therapy, such as therapy configured to reduce bladder contractions, during a portion of the bladder fill cycle and target delivery during phases of bladder filling more receptive to neurostimulation therapy, such as the second half, or third or fourth quartile, of the bladder fill cycle. The system can use a detected void event to predict when these phases occur during the fill cycle and time neurostimulation delivery accordingly or directly detect the phases of the fill cycle using one or more sensors. Although neurostimulation therapy is generally discussed as including electrical stimulation therapy, neurostimulation therapy may alternatively, or also include, drug delivery therapy.

A medical device, such as an implantable medical device (IMD) may implement the techniques described in this disclosure to deliver stimulation therapy to at least one nerve (e.g., spinal nerve or a pelvic floor nerve) to modulate activity of the nerve via at least one electrode electrically connected to the IMD. The electrical stimulation may be configured to modulate contraction of a detrusor muscle of the patient to cause a decrease in frequency of bladder contractions (to reduce incontinence) or an increase in the frequency of bladder contractions (to promote voiding). Reduction in frequency of bladder contractions may reduce urgency of voiding and may reduce urgency and/or urinary incontinence, and thereby at least partially alleviate bladder dysfunction.

The neurostimulation described herein may be targeted to manage bladder dysfunction, such as an overactive bladder, urgency, urinary incontinence, or even non-obstructive urinary retention. For example, the stimulation may be delivered to target tissue sites normally used to alleviate these types of dysfunction. Although the techniques are primarily described in this disclosure for managing bladder dysfunction, the techniques may also be applied to manage other pelvic floor disorders or disorders relating to other organs, tissues or nerves of the patient. For example, the devices, systems, and techniques described in this disclosure alternatively or additionally may be utilized to manage sexual dysfunction, pelvic pain, fecal urgency or fecal incontinence. Example nerves that may be targeted for therapy include sacral nerves, pudendal nerves, a dorsal nerve of the penis or clitoris, tibial nerves, sural nerves, sciatic nerves, the inferior rectal nerve, and peroneal or perineal nerves. Example organ systems that may be treated for dysfunction may include the large and small bowel, stomach and/or intestines, liver, and spleen, which may be modulated by delivering neurostimulation directly to the organs, to one or nerves innervating the organ, and/or blood supplies reaching the organs.

In the example of fecal incontinence, the IMD may deliver the neurostimulation therapy timed to the detection of a physiological marker indicative of an increased probability of an occurrence of a fecal incontinence (e.g., an increased patient activity level) or bowel fill level or activity level. The physiological state may include, for example, a magnitude of contraction of the anal sphincter, a patient activity level or a patient posture state.

FIG. 1 is a conceptual diagram illustrating an example system 10 that manages delivery of neurostimulation to patient 14 to manage bladder dysfunction, such as overactive bladder, urgency, or urinary incontinence. As described above, system 10 may be configured to deliver neurostimulation to the patient timed during a physiological cycle based on detection of one or more physiological markers. System 10 may terminate delivery of therapy, begin delivery of therapy, and/or withhold delivery of therapy based on one or more detected physiological markers. For example, system 10 may monitor one or more physiological markers to track and/or predict different phases of a physiological cycle that recurs within the patient. System 10 may then control delivery of neurostimulation to occur during the appropriate phase of the physiological cycle to reduce or eliminate one or more dysfunctional states related to the physiological cycle.

As shown in the example of FIG. 1, therapy system 10 includes an implantable medical device (IMD) 16 (e.g., an example medical device), which is coupled to leads 18, 20, and 28 and sensor 22. System 10 also includes an external programmer 24, which is configured to communicate with IMD 16 via wireless communication. IMD 16 generally operates as a therapy device that delivers neurostimulation (e.g., electrical stimulation in the example of FIG. 1) to, for example, a target tissue site proximate a spinal nerve, a sacral nerve, a pudendal nerve, dorsal genital nerve, a tibial nerve, an inferior rectal nerve, a perineal nerve, or other pelvic nerves, or branches of any of the aforementioned nerves. IMD 16 provides electrical stimulation to patient 14 by generating and delivering a programmable electrical stimulation signal (e.g., in the form of electrical pulses or an electrical waveform) to a target a therapy site near lead 28 and, more particularly, near electrodes 29A-29D (collectively referred to as "electrodes 29") disposed proximate to a distal end of lead 28.

IMD 16 may be surgically implanted in patient 14 at any suitable location within patient 14, such as near the pelvis. In some examples, IMD 16 may be implanted in a subcutaneous location in the side of the lower abdomen or the side of the lower back or upper buttocks. IMD 16 has a biocompatible housing, which may be formed from titanium, stainless steel, a liquid crystal polymer, or the like. The proximal ends of leads 18, 20, and 28 are both electrically and mechanically coupled to IMD 16 either directly or indirectly, e.g., via respective lead extensions. Electrical conductors disposed within the lead bodies of leads 18, 20, and 28 electrically connect sense electrodes (e.g., electrodes 19A, 19B, 21A, and 21B) and stimulation electrodes, such as electrodes 29, to a sensing module and a stimulation delivery module (e.g., a stimulation generator) within IMD 16. In the example of FIG. 1, leads 18 and 20 carry electrodes 19A, 19B (collective referred to as "electrodes 19") and electrodes 21A, 21B (collectively referred to as "electrodes 21"), respectively. As described in further detail below, electrodes 19 and 21 may be positioned for sensing an impedance of bladder 12, which may increase as the volume of urine within bladder 12 increases. In some examples, system 10 may include electrodes (such as electrodes 19 and 21), a strain gauge, one or more accelerometers, ultrasound sensors, optical sensors, or any other sensor capable of detecting contractions of bladder 12, pressure or volume of bladder 12, or any other indication of the fill cycle of bladder 12 and/or possible bladder dysfunctional states.

In other examples, system 10 may use sensors other than electrodes 19 and 21 for sensing bladder volume, or not use any sensors at all. For example, external programmer 24 may receive user input identifying a voiding event, perceived level of fullness, or any other indication of a physiological marker associated with the physiological cycle. The user input may be in the form of a voiding journal analyzed by external programmer 24 or IMD 16 or individual user inputs associated with respective voiding events, leakage, or any other event related to a physiological cycle. External programmer 24 and/or IMD 16 may use this user input to generate estimated fill cycles and determine phases of the fill cycle to deliver neurostimulation and withhold stimulation. In other words, one or more physiological markers may be identified from user input. The user input may be in addition to or instead of sensors such as electrodes 19A and 21A for detecting a physiological marker.

One or more medical leads, e.g., leads 18, 20, and 28, may be connected to IMD 16 and surgically or percutaneously tunneled to place one or more electrodes carried by a distal end of the respective lead at a desired nerve or muscle site, e.g., one of the previously listed target therapy sites such as a tissue site proximate a spinal (e.g., sacral) or pudendal nerve. For example, lead 28 may be positioned such that electrodes 29 deliver electrical stimulation to a spinal, sacral or pudendal nerve to reduce a frequency and/or magnitude of contractions of bladder 12. Additional electrodes of lead 28 and/or electrodes of another lead may provide additional stimulation therapy to other nerves or tissues as well. In FIG. 1, leads 18 and 20 are placed proximate to an exterior surface of the wall of bladder 12 at first and second locations, respectively. In other examples of therapy system 10, IMD 16 may be coupled to more than one lead that includes electrodes for delivery of electrical stimulation to different stimulation sites within patient 14, e.g., to target different nerves.

In the example shown in FIG. 1, leads 18, 20, 28 are cylindrical. Electrodes 19, 20, 29 of leads 18, 20, 28, respectively, may be ring electrodes, segmented electrodes, partial ring electrodes or any suitable electrode configuration. Segmented and partial ring electrodes each extend along an arc less than 360 degrees (e.g., 90-120 degrees) around the outer perimeter of the respective lead 18, 20, 28. In some examples, segmented electrodes 29 of lead 28 may be useful for targeting different fibers of the same or different nerves to generate different physiological effects (e.g., therapeutic effects). In examples, one or more of leads 18, 20, 28 may be, at least in part, paddle-shaped (e.g., a "paddle" lead), and may include an array of electrodes on a common surface, which may or may not be substantially flat.

In some examples, one or more of electrodes 19, 20, 29 may be cuff electrodes that are configured to extend at least partially around a nerve (e.g., extend axially around an outer surface of a nerve). Delivering electrical stimulation via one or more cuff electrodes and/or segmented electrodes may help achieve a more uniform electrical field or activation field distribution relative to the nerve, which may help minimize discomfort to patient 14 that results from the delivery of electrical stimulation. An electrical field may define the volume of tissue that is affected when the electrodes 19, 20, 29 are activated. An activation field represents the neurons that will be activated by the electrical field in the neural tissue proximate to the activated electrodes.

The illustrated numbers and configurations of leads 18, 20, and 28 and electrodes carried by leads 18, 20, and 28 are merely exemplary. Other configurations, e.g., numbers and positions of leads and electrodes are also contemplated. For example, in other implementations, IMD 16 may be coupled to additional leads or lead segments having one or more electrodes positioned at different locations proximate the spinal cord or in the pelvic region of patient 14. The additional leads may be used for delivering different stimulation therapies or other electrical stimulations to respective stimulation sites within patient 14 or for monitoring at least one physiological parameter of patient 14.

In accordance with some examples of the disclosure, IMD 16 delivers electrical stimulation to at least one of a spinal nerve (e.g., a sacral nerve), a pudendal nerve, dorsal genital nerve, a tibial nerve, an inferior rectal nerve, or a perineal nerve to provide a therapeutic effect that reduces or eliminates a dysfunctional state such as overactive bladder. The desired therapeutic effect may be an inhibitory physiological response related to voiding of patient 14, such as a reduction in bladder contraction frequency by a desired level or degree (e.g., percentage). In particular, IMD 16 may deliver stimulation via at least one of electrodes 29 during a second phase of the bladder fill cycle during which the nerves or targeted tissue respond efficaciously to stimulation therapy. IMD 16 may determine this second phase based on one or more physiological markers such as a bladder fill level (e.g., volume or pressure) or time since the previous voiding event. IMD 16 may then control the therapy delivery module to withhold stimulation delivery during other phases, such as a first phase subsequent to the voiding event and prior to the second phase during which stimulation is delivered.

The stimulation program may define various parameters of the stimulation waveform and electrode configuration which result in a predetermined stimulation intensity being delivered to the targeted nerve or tissue. In some examples, the stimulation program defines parameters for at least one of a current or voltage amplitude of the stimulation signal, a frequency or pulse rate of the stimulation, the shape of the stimulation waveform, a duty cycle of the stimulation, a pulse width of the stimulation, and/or the combination of electrodes 29 and respective polarities of the subset of electrodes 29 used to deliver the stimulation. Together, these stimulation parameter values may be used to define the stimulation intensity (also referred to herein as a stimulation intensity level). In some examples, if stimulation pulses are delivered in bursts, a burst duty cycle also may contribute to stimulation intensity. Also, independent of intensity, a particular pulse width and/or pulse rate may be selected from a range suitable for causing the desired therapeutic effect after stimulation is terminated and, optionally, during stimulation. In addition, as described herein, a period during which stimulation is delivered may include on and off periods (e.g., a duty cycle or bursts of pulses) where even the short inter-pulse durations of time when pulses are not delivered are still considered part of the delivery of stimulation. A period during which system 10 withholds stimulation delivery is a period in which no stimulation program is active for IMD 16 (e.g., IMD 16 is not tracking pulse durations or inter-pulse durations that occur as part of the electrical stimulation delivery scheme). In other words, the withholding period is based on one or more physiological markers instead of a pre-defined pulse frequency, burst frequency, or duty cycle for an electrical stimulation signal or set of pulses. Typically, a period during which system 10 withholds neurostimulation is on the order of minutes or hours, not tenths of a second or several seconds.

In addition to the above stimulation parameters, the stimulation may be defined by other characteristics, such as a time for which stimulation is delivered, a time for which stimulation is terminated, and times during which stimulation is withheld. These times may be absolute or linked to the physiological cycle and/or one or more physiological markers associated with the physiological cycle. In some examples, IMD 16 may be configured to deliver different types of stimulation therapy at different times during the physiological cycle. For example, IMD 16 may deliver stimulation configured to reduce or eliminate bladder contractions to promote urine retention and/or increased bladder capacity and then deliver stimulation configured to promote urination (e.g., increased frequency or magnitude of bladder contractions) for a user requested voiding event or once a voiding event is detected to have begun.

System 10 may also include an external programmer 24, as shown in FIG. 1. Programmer 24 may be a clinician programmer or patient programmer. In some examples, programmer 24 may be a wearable communication device, with a therapy request input integrated into a key fob or a wrist watch, handheld computing device, computer workstation, or networked computing device. Programmer 24 may include a user interface that is configured to receive input from a user (e.g., patient 14, a patient caretaker or a clinician). In some examples, the user interface includes, for example, a keypad and a display, which may for example, be a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 and/or ICD 16 remotely via a networked computing device.

A user, such as a physician, technician, surgeon, electrophysiologist, or other clinician, may also interact with programmer 24 or another separate programmer (not shown), such as a clinician programmer, to communicate with IMD 16. Such a user may interact with a programmer to retrieve physiological or diagnostic information from IMD 16. The user may also interact with a programmer to program IMD 16, e.g., select values for the stimulation parameter values with which IMD 16 generates and delivers stimulation and/or the other operational parameters of IMD 16, such as magnitudes of stimulation energy, user requested periods for stimulation or periods to prevent stimulation, or any other such user customization of therapy. As discussed herein, the user may also provide input to external programmer 24 indicative of physiological events (for physiological markers) such as bladder fill level perception and void events.

For example, the user may use a programmer to retrieve information from IMD 16 regarding the contraction frequency of bladder 12 and/or voiding events. As another example, the user may use a programmer to retrieve information from IMD 16 regarding the performance or integrity of IMD 16 or other components of system 10, such as leads 18, 20, and 28, or a power source of IMD 16. In some examples, this information may be presented to the user as an alert if a system condition that may affect the efficacy of therapy is detected.

Patient 14 may, for example, use a keypad or touch screen of programmer 24 to request IMD 16 to deliver or terminate the electrical stimulation, such as when patient 14 senses that a leaking episode may be imminent or when an upcoming void may benefit from terminating therapy that promotes urine retention. In this way, patient 14 may use programmer 24 to provide a therapy request to control the delivery of the electrical stimulation "on demand," e.g., when patient 14 deems the second stimulation therapy desirable. This request may be a therapy trigger event used to terminate electrical stimulation.

Programmer 24 may provide a notification to patient 14 when the electrical stimulation is being delivered or notify patient 14 of the prospective termination of the electrical stimulation. In addition, notification of termination may be helpful so that patient 14 knows that a voiding event may be more probable and/or the end of the fill cycle is nearing such that the bladder should be emptied (e.g., the patient should visit a restroom). In such examples, programmer 24 may display a visible message, emit an audible alert signal or provide a somatosensory alert (e.g., by causing a housing of programmer 24 to vibrate). In other examples, the notification may indicate when therapy is available (e.g., a countdown in minutes, or indication that therapy is ready) during the physiological cycle. In this manner, programmer 24 may wait for input from patient 14 prior to terminating the electrical stimulation that reduces bladder contraction or otherwise promotes urine retention. Patient 14 may enter input that either confirms termination of the electrical stimulation so that the therapy stops for voiding purposes, confirms that the system should maintain therapy delivery until patient 14 can void, and/or confirms that patient 14 is ready for another different stimulation therapy that promotes voiding during the voiding event.

In the event that no input is received within a particular range of time when a voiding event is predicted, programmer 24 may wirelessly transmit a signal that indicates the absence of patient input to IMD 16. IMD 16 may then elect to continue stimulation until the patient input is received, or terminate stimulation to avoid tissue damage, based on the programming of IMD 16. As described herein, the termination or continuation of electrical stimulation may be responsive to other physiological markers.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

In one example described herein, system 10 includes one or more processors (e.g., processors or control modules contained in external programmer 24 and/or IMD 16) configured to monitor a fill cycle of bladder 12 of patient 14, where the fill cycle starts after completion of a first voiding event and ends at the completion of a second voiding event. In other examples, the fill cycle may be described as starting upon the beginning of a voiding event and ending upon detection of the beginning of the next fill cycle. A processor may control IMD 16 to withhold delivery of neurostimulation therapy to patient 14 for a first phase including the start of the fill cycle, wherein the neurostimulation therapy is configured to inhibit contraction of bladder 12. Since bladder 12 (or the associated detrusor muscle or related nerves) may not be reactive to neurostimulation during the first phase of the fill cycle, IMD 16 may withhold the stimulation during this first phase. The processor may then determine, based on one or more physiological markers associated with the fill cycle (e.g., the previous voiding event or an indication of the current bladder fill level), a second phase of the fill cycle during which the neurostimulation therapy will be delivered to patient 14. This determination may include the duration of the second phase and when the second phase is to begin within the fill cycle (e.g., the timing of the second phase after the voiding event or prior to the next predicted voiding event). As described herein, the second phase for neurostimulation delivery may immediately follow the first phase where IMD 16 withholds stimulation. The processor of system 10 may then control IMD 16 to deliver neurostimulation therapy to patient 14 during the second phase of the fill cycle.

System 10 may terminate the second phase of the fill cycle prior to the next voiding event. This termination may help patient 14 complete the voiding event and void urine from bladder 12. However, the second phase and stimulation delivery may continue until the end of a voiding even in some examples. The second phase may be determined to at least start prior to a predicted start of dysfunctional events related to the fill cycle, such as frequent, coordinated, and/or strong detrusor muscle contractions. In this manner, the stimulation delivered during the second phase may preemptively reduce or even eliminate these dysfunctional events that may result in incontinence. System 10 may determine the second phase to overlap during a dysfunctional phase when dysfunction is predicted to occur. In other example, system 10 may deliver stimulation during the second phase and terminate the second phase prior to predicted dysfunction when the stimulation can effectively quiet bladder activity.

As discussed further below with respect to FIGS. 7A-10B, the placement of the second phase within the fill cycle can be made for effective delivery of stimulation. In one example, the third quartile of the fill cycle may include or comprise the second phase. In another example, the fourth quartile of the fill cycle may include or comprise the second phase. Therefore, the second phase may be located at least partially within or fully within these quartiles of the fill cycle. In other examples, the first half of the fill cycle may include the first phase during which system 10 withholds stimulation, and the second half of the fill cycle may include the second phase during which system 10 delivers stimulation therapy to patient 14. System 10 may, in some examples, deliver additional types of neurostimulation after the second phase, such as stimulation configured to promote bladder contraction during a voiding event.

In some examples, system 10 is configured to detect at the voiding events and, responsive to the detection, control IMD 16 to terminate delivery of the neurostimulation therapy. Therefore, the first phase of the fill cycle would not include neurostimulation delivered to patient 14. However, as discussed above, external programmer 24 and/or IMD 16 may control delivery of different types of neurostimulation after the second phase stimulation has been terminated. For example, IMD 16 may deliver therapy during the voiding event that promotes voiding, such as promotion of detrusor muscle contraction.

System 10 may determine the different phases of a physiological cycle (e.g., the bladder fill cycle) based on different factors and using different inputs in different examples. In this manner, system 10 may predict durations and times of the physiological cycle and durations and times of the different phases for future cycles in order to time delivery and withholding of stimulation therapy to physiological markers. In one example, system 10 determines the various phases of the physiological cycle based on one or more previous physiological cycles. This historical data from the previous physiological cycles may allow the system to predict when to withhold delivery of stimulation and when to deliver stimulation in order to treat one or more dysfunctional events associated with the cycle. For example, a processor of system 10 may be configured to determine when the second phase (e.g., when stimulation is delivered) of the bladder fill cycle begins by tracking a time period from the last voiding event that was detected. System 10 compares the time period to a fill time threshold which is the threshold in the fill cycle at which the second phase is to begin. Responsive to the time period exceeding the fill time threshold, system 10 may initiate the second phase of the fill cycle. The fill time threshold may be a percentage or fraction of the total fill time of the fill cycle or an absolute amount of time from the beginning of the cycle or to the predicted end of the fill cycle.

In some examples, system 10 is configured to estimate the fill time threshold based on respective durations of a plurality of previous fill cycles of patient 14. The previous fill cycles may be used to establish typical cycle durations, from which the fill time threshold can be calculated. For example, system 10 may calculate the fill time threshold by calculating an average of the respective durations of the plurality of previous fill cycles, determining an estimated second phase duration based on the average, and determining the fill time threshold as an initiation point for the second phase based on the average of the respective durations of the plurality of previous fill cycles. In other examples, a median, rolling average, weighted average, or some other estimation of the typical duration of a fill cycle may be used by system 10. The second phase duration may be calculated as a percentage of the estimated duration of the fill cycle and placed within the future cycle based on percentages of time or absolute times from the beginning of the cycle, end of the cycle, or predicted dysfunctional phase during which a dysfunctional event is predicted to occur. System 10 may also estimate durations and timing of one or more dysfunctional phases within the physiological cycle based on previously detected dysfunctional events.

As an alternative to predicting future phases of a physiological cycle based on previous cycles of patient 14, system 10 may utilize direct detection of a fill level of bladder 12 as physiological markers (e.g., instead of or in addition to voiding events). System 10 may be configured to determine the second phase of the bladder fill cycle for neurostimulation delivery by detecting a magnitude of the fill level, comparing the magnitude of the fill level to a threshold, and, responsive to the magnitude of the fill level exceeding the threshold, initiating the second phase of the fill cycle. For example, if the second phase is to begin when at the midpoint of the bladder fill cycle, system 10 may determine the threshold to be half of the magnitude change for the fill cycle during the entire fill cycle. The threshold may be a percentage of a total fill level such as a percentage of a bladder volume, pressure, singular dimension such as diameter. The threshold may also be linked to a physiological parameter indicative of the fill level such as muscle activity via an electromyogram (EMG), nerve activity, or other indication.

The magnitude of the fill level may be a physiological marker for the bladder fill cycle. In one example, system 10 may detect the magnitude of the fill level by detecting a pressure level of bladder 14 (e.g., via sensor 22). For example, one or more pressure or stretch sensors may be attached to the exterior of bladder 14 or implanted within the bladder. As another example, system 10 may detect the magnitude of the fill level by detecting an impedance level of bladder 14, such as by monitoring the impedance between electrodes 19 and 21 of FIG. 1.

IMD 16 can detect a contraction of bladder 12 using any suitable technique, such as based on a sensed physiological parameter that can be a physiological marker for the physiological cycle. One example physiological parameter is an impedance of bladder 12. In the example shown in FIG. 1, IMD 16 may determine impedance of bladder 12 using a four-wire (or Kelvin) measurement technique. In other examples, IMD 16 may measure bladder impedance using a two-wire sensing arrangement. In either case, IMD 16 may transmit an electrical measurement signal, such as a current, through bladder 12 via leads 18 and 20, and determine impedance of bladder 12 based on the transmitted electrical signal. Such an impedance measurement may be utilized to determine response of contractions of bladder 12 during the electrical stimulation or after termination of the electrical stimulation, to determine a fullness of bladder 12, or the like. Although fullness may be a physiological state indicative of the need for the desired therapeutic effect, fullness may also indicate that the frequency of bladder contractions will increase to void bladder 12.

In the example four-wire arrangement shown in FIG. 1, electrodes 19A and 21A and electrodes 19B and 21B, may be located substantially opposite each other relative to the center of bladder 12. For example, electrodes 19A and 21A may be placed on opposing sides of bladder 12, either anterior and posterior or left and right. In FIG. 1, electrodes 19 and 21 are shown placed proximate to an exterior surface of the wall of bladder 12. In some examples, electrodes 19 and 21 may be sutured or otherwise affixed to the bladder wall. In other examples, electrodes 19 and 21 may be implanted within the bladder wall. To measure the impedance of bladder 12, IMD 16 may source an electrical signal, such as current, to electrode 19A via lead 18, while electrode 21A via lead 20 sinks the electrical signal. IMD 16 may then determine the voltage between electrode 19B and electrode 21B via leads 18 and 20, respectively. IMD 16 determines the impedance of bladder 12 using a known value of the electrical signal sourced the determined voltage.

In other examples, electrodes 19 and 21 may be used to detect an EMG of the detrusor muscle. This EMG may be used to determine the frequency of bladder contractions and the physiological state of patient 14. The EMG may also be used to detect the strength of the bladder contractions in some examples. As an alternative, or in addition, to an EMG, a strain gauge or other device may be used to detect the status of bladder 12, e.g., by sensing forces indicative of bladder contractions.

In the example of FIG. 1, IMD 16 also includes a sensor 22 for detecting changes in the contraction of bladder 12. Sensor 22 may include, for example, a pressure sensor for detecting changes in bladder pressure, electrodes for sensing pudendal or sacral afferent nerve signals, electrodes for sensing urinary sphincter EMG signals (or anal sphincter EMG signals in examples in which system 10 provides therapy to manage fecal urgency or fecal incontinence), or any combination thereof. In examples in which sensor 22 is a pressure sensor, the pressure sensor may be a remote sensor that wirelessly transmits signals to IMD 16 or may be carried on one of leads 18, 20, or 28 or an additional lead coupled to IMD 16. In some examples, IMD 16 may determine whether a contraction frequency of bladder 12 has occurred based on a pressure signal generated by sensor 22.

In examples in which sensor 22 includes one or more electrodes for sensing afferent nerve signals, the sense electrodes may be carried on one of leads 18, 20, or 28 or an additional lead coupled to IMD 16. In examples in which sensor 22 includes one or more sense electrodes for generating a urinary sphincter EMG, the sense electrodes may be carried on one of leads 18, 20, or 28 or additional leads coupled to IMD 16. In any case, in some examples, IMD 16 may control the timing of the delivery of the electrical stimulation based on input received from sensor 22.

Sensor 22 may comprise a patient motion sensor that generates a signal indicative of patient activity level or posture state. In some examples, IMD 16 may terminate the delivery of the electrical stimulation to patient 14 upon detecting a patient activity level exceeding a particular threshold based on the signal from the motion sensor. The patient activity level that is greater than or equal to a threshold (which may be stored in a memory of IMD 16) may indicate that there is an increase in the probability that an involuntary voiding event will occur, and, therefore, system 10 should deliver electrical stimulation during the second phase or even begin the second phase early in some examples. In other examples, IMD 16 may use sensor 22 to identify posture states known to require the desired therapeutic effect. For example, patient 14 may be more prone to an involuntary voiding event when patient 14 is in an upright posture state compared to a lying down posture state. In any event, electrodes 19 and 21 and sensor 22 may be configured to detect voiding events and/or the magnitude of a fill level of bladder 12 during the fill cycle. Any of these detected features from patient 14 may be a physiological marker used by system 10 to determine when to deliver and withhold stimulation therapy.

As discussed above, system may monitor the fill cycle of bladder 12 by detecting subsequent voiding events over time. In some examples, system 10 may detect voiding events by receiving an indication of a user input (e.g., via external programmer 24) representative of an occurrence of a voiding event. In other words, external programmer 24 may receive input from the user identifying that a voiding event occurred, the beginning of a voiding event, and/or the end of the voiding event. In other examples, system 10 may automatically detect voiding events without receiving user input via external programmer 24. System 10 may instead detect voiding events by detecting at least one of a pressure of the bladder, a flow of urine from the bladder, a wetness of an article external of the patient, a volume of the bladder, an electromyogram (EMG) signal, a nerve recording, a posture change, a physical location of the patient within a structure such as a house or care facility, or a toilet use event. Some sensors external to patient 14 may communicate with external programmer 24 and/or IMD 16 to provide this information indicative of likely voiding events. For example, wetness may be detected by a moisture sensor (e.g., electrical impedance or chemical sensor) embedded in an undergarment worn by the patient and transmitted to IMD 16 or external programmer 24. Similarly, a toilet may include a presence sensor that detects when a patient is using the toilet (e.g., an infrared sensor, thermal sensor, or pressure senor) and transmits a signal indicating the presence of the patient to IMD 16 or external programmer 24. In this manner, non-invasively obtained data may provide information indicative of voiding events without implanted sensors.

These examples of bladder therapy described in FIG. 1 are examples of therapy delivered based on a physiological marker associated with a physiological cycle to treat a dysfunctional state of the physiological cycle. However, such processes may also be used by system 10 to treat other dysfunctions and conditions of patient 14. In one example, one or more processors of system 10 may be configured to detect a physiological marker that occurs prior in time to a dysfunctional phase of a physiological cycle, wherein a dysfunctional state of the physiological cycle occurs during the dysfunctional phase without treatment (e.g., absent stimulation therapy the dysfunctional state may occur during the dysfunctional phase). Responsive to detecting the physiological marker, system 10 may initiate a first phase of the physiological cycle having a duration of time and withhold delivery of neurostimulation therapy for the duration of time of the first phase. Responsive to the first phase elapsing, a processor of system 10 may control a therapy delivery module (e.g., a therapy delivery module of IMD 16) to deliver neurostimulation therapy during a second phase that begins prior to the dysfunctional phase. In this manner, the neurostimulation therapy is configured to treat the dysfunctional state.

In some examples, the second phase at least partially overlaps with the dysfunctional phase. In other examples, the second phase ends prior to the dysfunctional phase, and responsive to the second phase ending, system 10 is configured to terminate delivery of the neurostimulation therapy. Generally, delivery of the neurostimulation therapy during the second phase of the physiological cycle one or reduces or eliminates the dysfunctional state of the physiological cycle. In some examples, delivery of the neurostimulation therapy during a first physiological cycle may even reduce or eliminate the dysfunctional state of a second physiological cycle subsequent to the prior physiological cycle without delivery of the neurostimulation therapy during the second physiological cycle. In other words, delivery of the neurostimulation therapy during an appropriate time in the physiological cycle, such as during the second phase, may retrain organs and/or nerves to function properly again.

As discussed above, the dysfunctional state may include a bladder dysfunction. For bladder dysfunctions, the physiological marker may include a fill level of the bladder, a detrusor contraction during the first phase of the physiological cycle, and/or a voiding event. In other examples, the dysfunctional state may include a colon dysfunction. As described herein, neurostimulation therapy includes at least one of electrical stimulation or drug therapy.

Figure 2A:
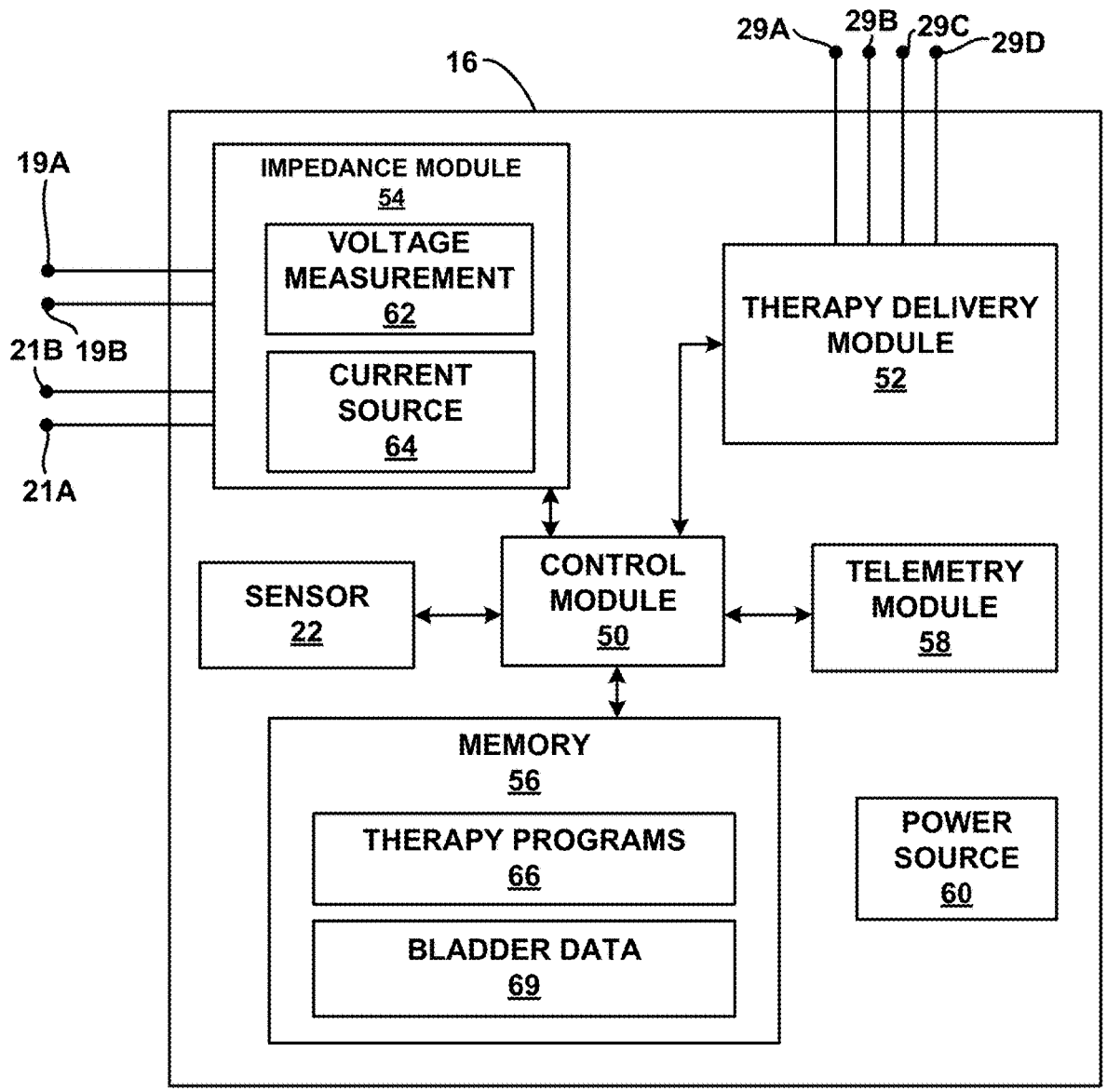
FIGS. 2A and 2B are block diagrams illustrating example configurations of implantable medical devices (IMDs) which may be utilized in the system of FIG. 1.
Figure 2B:
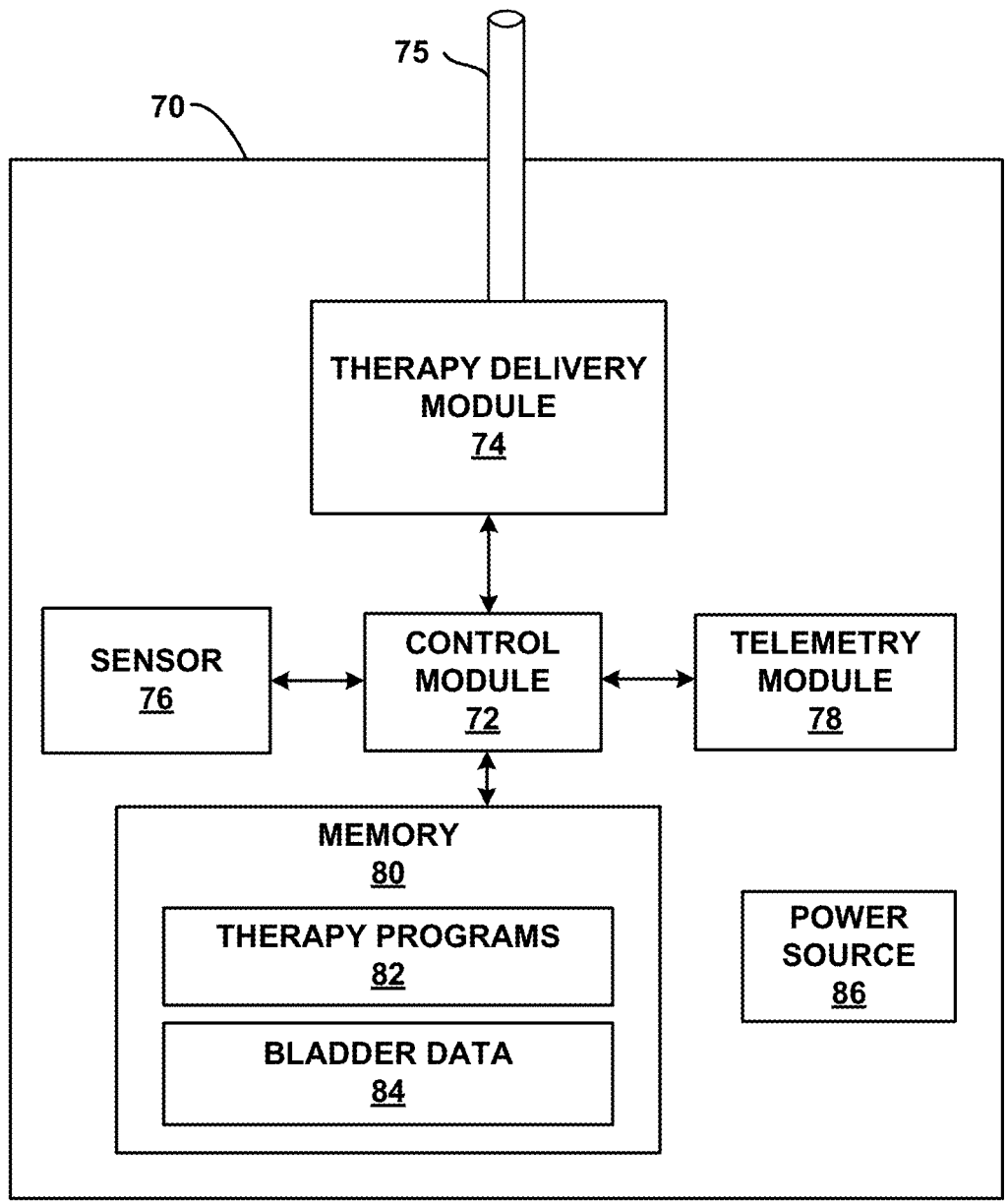

FIGS. 2A and 2B are block diagram illustrating example configurations of different types of implantable medical devices (IMDs) which may be utilized in the system of FIG. 1. As shown in FIG. 2A, IMD 16 includes sensor 22, control module 50, therapy delivery module 52, impedance module 54, memory 56, telemetry module 58, and power source 60. In other examples, IMD 16 may include a greater or fewer number of components. For example, in some examples, such as examples in which IMD 16 deliver the electrical stimulation in an open-loop manner, IMD 16 may not include sensor 22 (e.g., a pressure sensor or electrical signal sensors) and/or impedance module 54. In other examples, physiological markers may be provided via patient input on an external programmer if no sensors (e.g., sensor 22 and/or impedance module 54) is included by IMD 16.

In general, IMD 16 may comprise any suitable arrangement of hardware, alone or in combination with software and/or firmware, to perform the techniques attributed to IMD 16 and control module 50, therapy delivery module 52, impedance module 54, and telemetry module 58 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 16 also, in various examples, may include a memory 56, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although control module 50, therapy delivery module 52, impedance module 54, and telemetry module 58 are described as separate modules, in some examples, control module 50, therapy delivery module 52, impedance module 54, and telemetry module 58 are functionally integrated. In some examples, control module 50, therapy delivery module 52, impedance module 54, and telemetry module 58 correspond to individual hardware units, such as ASICs, DSPs, FPGAs, or other hardware units.

Memory 56 stores therapy programs 66 that specify stimulation parameter values for the electrical stimulation provided by IMD 16. Therapy programs 66 may also store information regarding determining and using physiological markers, information regarding physiological cycles and/or dysfunctional states, or any other information required by IMD 16 to deliver stimulation therapy based on one or more physiological markers. In some examples, memory 56 also stores bladder data 69, which control module 50 may use for controlling the timing of the delivery of the electrical stimulation (e.g., phases of physiological cycles that define when to deliver and withhold stimulation). For example, bladder data 69 may include threshold values or baseline values for at least one of bladder impedance, bladder pressure, sacral or pudendal afferent nerve signals, bladder contraction frequency, or external urinary sphincter EMG templates for use as physiological markers for an associated physiological cycle.

Memory 56 may also store instructions for execution by control module 50, in addition to stimulation programs 66 and bladder data 69. Information related to sensed bladder contractions, bladder impedance and/or posture of patient 14 may be recorded for long-term storage and retrieval by a user, and/or used by control module 50 for adjustment of stimulation parameters (e.g., amplitude, pulse width, and pulse rate) or for use as a physiological marker. In some examples, memory 56 includes separate memories for storing instructions, electrical signal information, stimulation programs 66, and bladder data 69. In other examples, control module 50 select new stimulation parameters for a stimulation program 66 or new stimulation program from stimulation programs 66 to use in the delivery of the electrical stimulation based on patient input and/or monitored physiological states after termination of the electrical stimulation.

Generally, therapy delivery module 52 generates and delivers electrical stimulation under the control of control module 50. As used herein, controlling the delivery of electrical stimulation may also include controlling the termination of stimulation to achieve the different stimulation and non-stimulation phases of the physiological cycle. In some examples, control module 50 controls therapy delivery module 52 by accessing memory 56 to selectively access and load at least one of stimulation programs 66 to therapy delivery module 52. For example, in operation, control module 50 may access memory 56 to load one of stimulation programs 66 to therapy delivery module 52.

By way of example, control module 50 may access memory 56 to load one of stimulation programs 66 to therapy delivery module 52 for delivering the electrical stimulation to patient 14. A clinician or patient 14 may select a particular one of stimulation programs 66 from a list using a programming device, such as programmer 24 or a clinician programmer. Control module 50 may receive the selection via telemetry module 58. Therapy delivery module 52 delivers the electrical stimulation to patient 14 according to the selected program for an extended period of time, such as minutes, hours, days, weeks, or until patient 14 or a clinician manually stops or changes the program.

Therapy delivery module 52 delivers electrical stimulation according to stimulation parameters. In some examples, therapy delivery module 52 delivers electrical stimulation in the form of electrical pulses. In such examples, relevant stimulation parameters may include a voltage amplitude, a current amplitude, a pulse rate, a pulse width, a duty cycle, or the combination of electrodes 29 that therapy delivery module 52 uses to deliver the stimulation signal. In other examples, therapy delivery module 52 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 29 therapy delivery module 52 uses to deliver the stimulation signal.

In some examples, the stimulation parameters for the stimulation programs 66 may be selected to relax bladder 12, e.g., to reduce a frequency of contractions of bladder 12, after termination of the electrical stimulation. An example range of stimulation parameters for the electrical stimulation that are likely to be effective in treating bladder dysfunction, e.g., upon application to the spinal, sacral, pudendal, tibial, dorsal genital, inferior rectal, or perineal nerves, are as follows:

1. Frequency or pulse rate: between about 0.5 Hz and about 500 Hz, such as between about 1 Hz and about 250 Hz, between about 1 Hz and about 20 Hz, or about 10 Hz.
2. Amplitude: between about 0.1 volts and about 50 volts, such as between about 0.5 volts and about 20 volts, or between about 1 volt and about 10 volts. Alternatively, the amplitude may be between about 0.1 milliamps (mA) and about 50 mA, such as between about 0.5 mA and about 20 mA, or between about 1 mA and about 10 mA.
3. Pulse Width: between about 10 microseconds (µs) and about 5000 µs, such as between about 100 µs and about 1000 µs, or between about 100 µs and about 200 µs.

When IMD 16 is monitoring the fill level of the bladder to determine the status of the bladder fill cycle, control module 50 may monitor impedance of bladder 12 for a predetermined duration of time to detect contractions of bladder 12, and determine the baseline contraction frequency of bladder 12 by determining a number of contractions of bladder 12 in the predetermined duration of time. In other examples, electrodes 19 or 21 may be used to detect an EMG of the detrusor muscle to identify bladder contraction frequencies. Alternatively, a strain gauge sensor signal output or other measure of bladder contraction change may be used to detect the physiological state of bladder 12. Each of these alternative methods of monitoring the fill level and/or voiding event of bladder 12 may be used in some examples.

In the example illustrated in FIG. 2, impedance module 54 includes voltage measurement circuitry 62 and current source 64, and may include an oscillator (not shown) or the like for producing an alternating signal, as is known. In some examples, as described above with respect to FIG. 1, impedance module 54 may use a four-wire, or Kelvin, arrangement. As an example, control module 50 may periodically control current source 64 to, for example, source an electrical current signal through electrode 19A and sink the electrical current signal through electrode 21A. In some examples, for collection of impedance measurements, current source 64 may deliver electrical current signals that do not deliver stimulation therapy to bladder 12, e.g., sub-threshold signals, due to, for example, the amplitudes or widths of such signals and/or the timing of delivery of such signals. Impedance module 54 may also include a switching module (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Control module 50 determines an impedance value from the measure voltage values received from voltage measurement circuitry 52.

In other examples, control module 50 may monitor signals received from sensor 22 to detect contraction of bladder 12 and determine the baseline contraction frequency. In some examples, sensor 22 may be a pressure sensor for detecting changes in pressure of bladder 12, which control module 50 may correlate to contractions of bladder 12. Control module 50 may determine a pressure value based on signals received from sensor 22 and compare the determined pressure value to a threshold value stored in bladder data 69 to determine whether the signal is indicative of a contraction of bladder 12. In some implementations, control module 50 monitors pressure of bladder 12 to detect contractions of bladder 12 for a predetermined duration of time, and determines a contraction frequency of bladder 12 by calculating a number of contractions of bladder 12 in the predetermined time period.

In some examples, control module 50 may cause contraction frequency information to be stored as bladder data 69 in memory 56, and may utilize the changes to contraction frequency to track the fill level of the bladder fill cycle or otherwise track the status of the fill cycle. In some implementations, control module 50 may, automatically or under control of a user, determine the contraction frequency over the fill cycle. Control module 50 may determine that an increase in contraction frequency indicates a later stage, or phase, of the fill cycle. In some examples, control module 50 may track bladder contractions using EMG signals of patient 14. In some implementations, sensor 22 may include an EMG sensor, and control module 50 may generate an EMG from the received signals generated by sensor 22. Sensor 22 may be implanted proximate to a muscle which is active when bladder 12 is contracting, such as a detrusor muscle. Control module 50 may compare an EMG collected during the second time period to EMG templates stored as bladder data 69 (e.g., a short-term running average) to determine whether the contractions of bladder 12 are indicative of particular phases of the bladder fill cycle.

In other examples, sensor 22 may be a pressure sensor and control module 50 may monitor signals received from sensor 22 during at least a portion of the second time period to detect contraction of bladder 12. In some implementations, control module 50 substantially continuously monitors pressure of bladder 12, at least during the second time periods, to detect contraction of bladder 12, and determines a contraction frequency of bladder 12 by determining a number of contractions of bladder 12 in a specified time period. Sensor 22 may also provide longer-term changes in pressure to track the bladder fill status (e.g., increased bladder volume may correspond to increased bladder pressure).

In the example of FIG. 2, therapy delivery module 52 drives electrodes on a single lead 28. Specifically, therapy delivery module 52 delivers electrical stimulation to tissue of patient 14 via selected electrodes 29A-29D carried by lead 28. A proximal end of lead 28 extends from the housing of IMD 16 and a distal end of lead 28 extends to a target therapy site, such as a spinal nerve (e.g., an S3 nerve), or a therapy site within the pelvic floor, such as tissue sites proximate a sacral nerve, a pudendal nerve, a tibial nerve, a dorsal genital nerve, an inferior rectal nerve, a perineal nerve, a hypogastric nerve, a urinary sphincter, or any combination thereof. In other examples, therapy delivery module 52 may deliver electrical stimulation with electrodes on more than one lead and each of the leads may carry one or more electrodes. The leads may be configured as an axial lead with ring electrodes or segmented electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 16.

As previously described, sensor 22 may comprise a pressure sensor configured to detect changes in bladder pressure, electrodes for sensing pudendal or sacral afferent nerve signals, or electrodes for sensing external urinary sphincter EMG signals (or anal sphincter signals in examples in which IMD 16 provides fecal urgency or fecal incontinence therapy), or any combination thereof. Additionally, or alternatively, sensor 22 may comprise a motion sensor, such as a two-axis accelerometer, three-axis accelerometer, one or more gyroscopes, pressure transducers, piezoelectric crystals, or other sensors that generate a signal that changes as patient activity level or posture state changes. Control module 50 may detect a physiological marker indicative of point during a bladder fill cycle. Sensor 22 may also be a motion sensor that is responsive to tapping (e.g., by patient 14) on skin superior to IMD 16. Control module 50 may be configured to log patient input using this tapping method (e.g., tapping may indicate that a voiding event is occurring). Alternatively, or in addition, control module 50 may control therapy module 52 to deliver or terminate electrical stimulation delivery in response to the tapping or certain pattern of tapping.

In examples in which sensor 22 includes a motion sensor, control module 50 may determine a patient activity level or posture state based on a signal generated by sensor 22. This patient activity level may be, for example, sitting, exercising, working, running, walking, or any other activity of patient 14. For example, control module 50 may determine a patient activity level by sampling the signal from sensor 22 and determining a number of activity counts during a sample period, where each activity level of a plurality of activity levels is associated with respective activity counts. In one example, control module 50 compares the signal generated by sensor 22 to one or more amplitude thresholds stored within memory 56, and identifies each threshold crossing as an activity count. The physical activity may be indicative of a fill level, a voiding event, or any other physiological marker related to the bladder fill cycle.

In some examples, control module 50 may control therapy delivery module 52 to deliver or terminate the electrical stimulation based on patient input received via telemetry module 58. Telemetry module 58 includes any suitable hardware, firmware, software or any combination thereof for communicating with another device, such as programmer 24 (FIG. 1). Under the control of control module 50, telemetry module 58 may receive downlink telemetry, e.g., patient input, from and send uplink telemetry, e.g., an alert, to programmer 24 with the aid of an antenna, which may be internal and/or external. Control module 50 may provide the data to be uplinked to programmer 24 and the control signals for the telemetry circuit within telemetry module 58, and receive data from telemetry module 58.

Generally, control module 50 controls telemetry module 58 to exchange information with medical device programmer 24 and/or another device external to IMD 16. Control module 50 may transmit operational information and receive stimulation programs or stimulation parameter adjustments via telemetry module 58. Also, in some examples, IMD 16 may communicate with other implanted devices, such as stimulators, control devices, or sensors, via telemetry module 58.

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever electrical stimulation is to occur.

As shown in FIG. 2B, IMD 70 is similar to IMD 16 of FIG. 2A, but IMD 70 delivers neurostimulation to patient 14 in the form of drugs instead of electrical stimulation. IMD 70 includes control module 72 (e.g., similar to control module 50), therapy delivery module 74 coupled to catheter 75, sensor 76 (e.g., a pressure sensor similar to sensor 22 of FIG. 2A), telemetry module 78 (e.g., similar to telemetry module 58), memory 80 (e.g., similar to memory 56), and power source 86 (e.g., similar to power source 60. Although IMD 70 does not include impedance module 54, this or other module may be provided in some examples.

Therapy delivery module 74 may include a drug reservoir and drug pump that moves the drug from the reservoir, through catheter 75, and out to patient 14. In some examples, IMD 70 may include both a drug pump and electrical stimulation generator. Therapy programs 82 may include instructions for drug delivery that may be based on one or more physiological markers stored as bladder data 84. In this manner, control module 72 may predict when to deliver a bolus of drug to patient 14 based on a phase of a physiological cycle such as the bladder fill cycle, for example.

Figure 3:
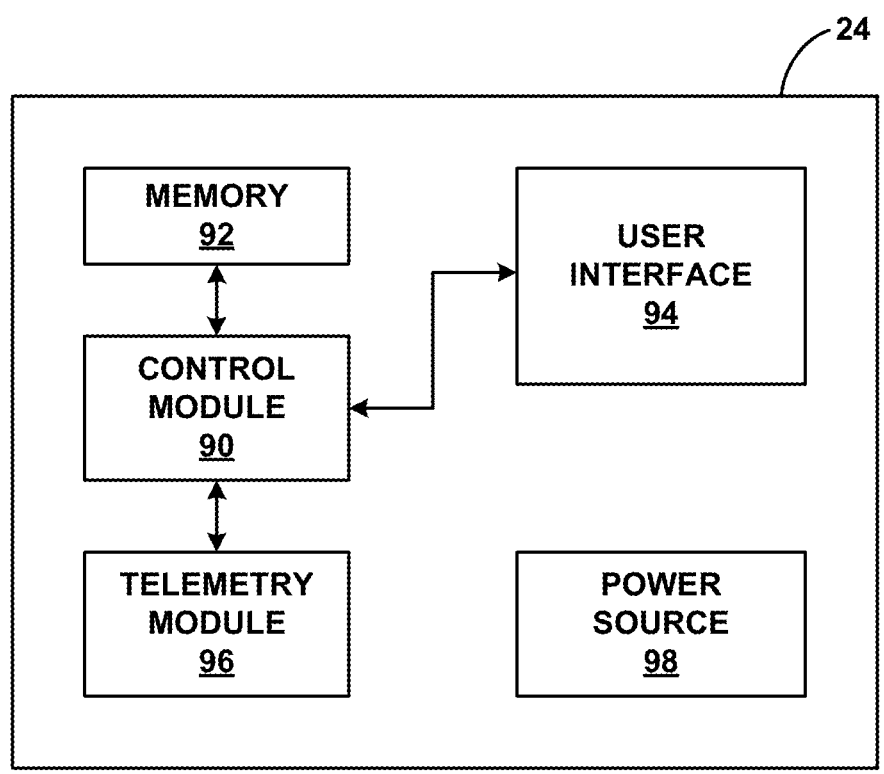
FIG. 3 is a block diagram illustrating an example configuration of an external programmer which may be utilized in the system of FIG. 1.

FIG. 3 is a block diagram illustrating an example configuration of an external programmer 24. While programmer 24 may generally be described as a hand-held computing device, the programmer may be a notebook computer, a cell phone, or a workstation, for example. As illustrated in FIG. 3, external programmer 24 may include a control module 90, memory 92, user interface 94, telemetry module 96, and power source 98. Memory 92 may store program instructions that, when executed by control module 90, cause control module 90 and external programmer 24 to provide the functionality ascribed to external programmer 24 throughout this disclosure.

In general, programmer 24 comprises any suitable arrangement of hardware, alone or in combination with software and/or firmware, to perform the techniques attributed to programmer 24, and control module 90, user interface 94, and telemetry module 96 of programmer 24. In various examples, programmer 24 may include one or more processors, such as one or more microprocessors, DSPs, ASICs, FPGAs, or any other equivalent integrated or discrete logic circuitry, as well as any combinations of such components. Programmer 24 also, in various examples, may include a memory 92, such as RAM, ROM, PROM, EPROM, EEPROM, flash memory, a hard disk, a CD-ROM, comprising executable instructions for causing the one or more processors to perform the actions attributed to them. Moreover, although control module 90 and telemetry module 96 are described as separate modules, in some examples, control module 90 and telemetry module 96 are functionally integrated. In some examples, control module 90 and telemetry module 96 and telemetry module 58 correspond to individual hardware units, such as ASICs, DSPs, FPGAs, or other hardware units.

Memory 92 may store program instructions that, when executed by control module 90, cause control module 90 and programmer 24 to provide the functionality ascribed to programmer 24 throughout this disclosure. In some examples, memory 92 may further include program information, e.g., stimulation programs defining the neurostimulation, similar to those stored in memory 56 of IMD 16. The stimulation programs stored in memory 92 may be downloaded into memory 56 of IMD 16.

User interface 94 may include a button or keypad, lights, a speaker for voice commands, a display, such as a liquid crystal (LCD), light-emitting diode (LED), or cathode ray tube (CRT). In some examples the display may be a touch screen. As discussed in this disclosure, control module 90 may present and receive information relating to electrical stimulation and resulting therapeutic effects via user interface 94. For example, control module 90 may receive patient input via user interface 94. The input may be, for example, in the form of pressing a button on a keypad or selecting an icon from a touch screen.

Control module 90 may also present information to the patient in the form of alerts related to delivery of the electrical stimulation to patient 14 or a caregiver, as described in more detail below, via user interface 94. Although not shown, programmer 24 may additionally or alternatively include a data or network interface to another computing device, to facilitate communication with the other device, and presentation of information relating to the electrical stimulation and therapeutic effects after termination of the electrical stimulation via the other device.

Telemetry module 96 supports wireless communication between IMD 16 and programmer 24 under the control of control module 90. Telemetry module 96 may also be configured to communicate with another computing device via wireless communication techniques, or direct communication through a wired connection. In some examples, telemetry module 96 may be substantially similar to telemetry module 58 of IMD 16 described above, providing wireless communication via an RF or proximal inductive medium. In some examples, telemetry module 96 may include an antenna, which may take on a variety of forms, such as an internal or external antenna.

Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 98 delivers operating power to the components of programmer 24. Power source 98 may include a battery and a power generation circuit to produce the operating power. In some examples, the battery may be rechargeable to allow extended operation.

Figure 4:
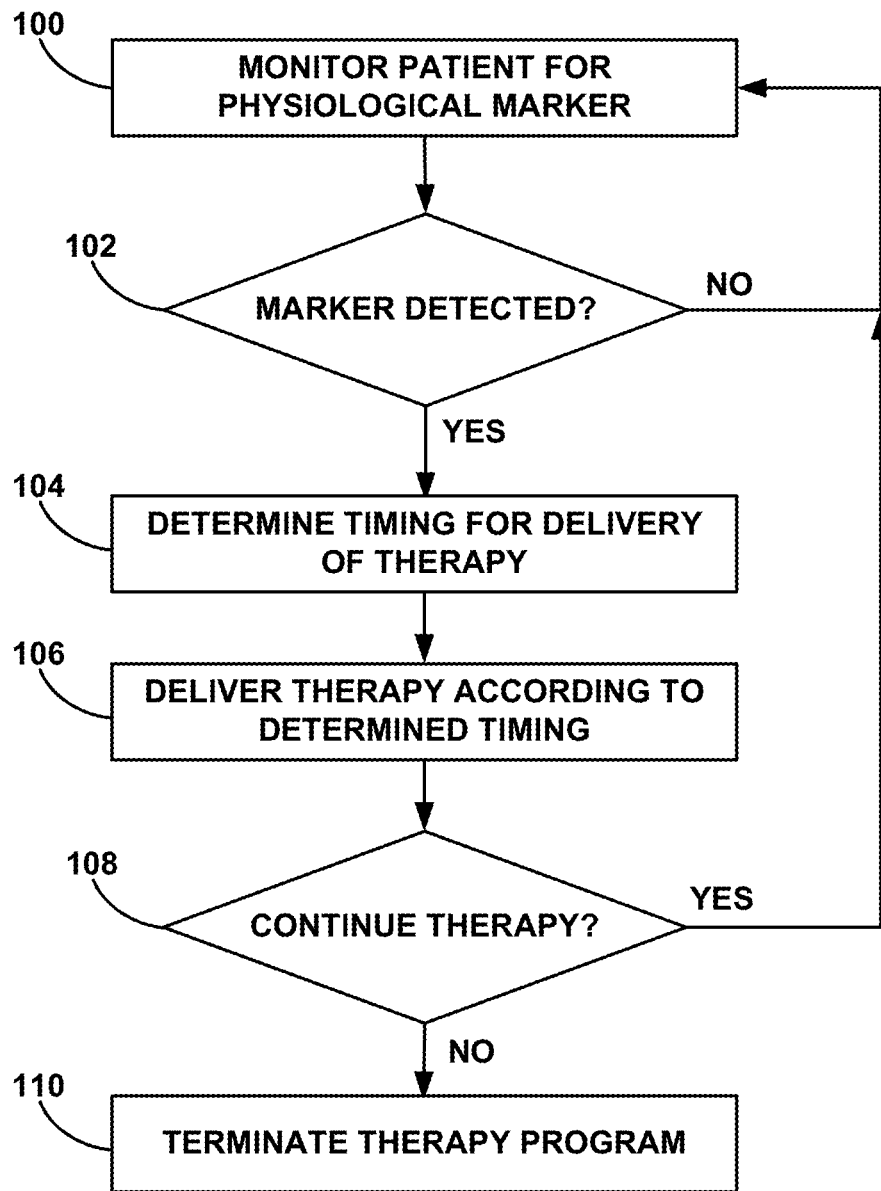
FIG. 4 is a flow diagram that illustrates an example technique for determining a timing for therapy delivery based on a physiological marker.

FIG. 4 is a flow diagram that illustrates an example technique for determining a timing for therapy delivery based on a physiological marker. The technique of FIG. 4 will be described with respect to control module 50 of IMD 16 for purposes of illustration. However, in other examples, control module 72 of IMD 70 or control module 90 of external programmer 24 may perform similar functions or employ a distributive functionality to with other devices (e.g., functionality split between external programmer 24 and IMD 16).

As shown in FIG. 4, control module 50 may monitor patient 14 for a physiological marker (100). The physiological marker may be associated with a dysfunctional state of patient 14. If control module 50 does not detect the marker ("NO" branch of block 102), control module 50 may continue to monitor for the marker (100). If control module 50 detects the marker ("YES" branch of block 102), control module 50 may determine timing for delivery of therapy after the physiological marker (104). For example, control module 50 may determine the duration of time between the marker and delivery of neurostimulation and/or the duration of the phase during which neurostimulation will be delivered. As discussed herein, control module 50 may determine the timing of therapy delivery based on previously detected or recorded dysfunctional states and whether the neurostimulation should be delivered prior to and/or during the dysfunctional state.

Control module 50 may then deliver the neurostimulation therapy according to the determined timing (106). If control module 50 is to continue delivering therapy to treat another predicted dysfunctional state ("YES" branch of block 108), control module 50 may continue to monitor patient 14 for the physiological marker (100). If control module 50 is to stop delivering therapy ("NO" branch of block 108), control module 50 terminates the therapy delivery program (110). The process of FIG. 4 may be applicable to physiological cycles that include a dysfunctional state such as a bladder fill cycle for patient 14 suffering from incontinence. However, control module 50 may track other physiological cycles or recurring events to predict when to deliver neurostimulation to treat an upcoming dysfunctional state. The process of FIG. 4, similar to the process of FIG. 5, may be suitable for treating dysfunction associated with organs other than the bladder, such as the large and small bowel, stomach and/or intestines, liver, or spleen, as some examples.

In some examples, control module 50 may withhold neurostimulation delivery during the first phase after detection of the physiological marker. In other examples, control module 50 may control the medical device to deliver a first neurostimulation therapy (or multiple different therapies) between the physiological marker and the neurostimulation timed to the marker. Control module 50 may transition from the first neurostimulation therapy to the second neurostimulation timed based on the physiological marker by changing one or more parameters of the first neurostimulation therapy according to the parameters of the second neurostimulation therapy. Control module 50 may change parameters such as at least one of a voltage amplitude, a current amplitude, a pulse frequency, a stimulation waveform frequency, a pulse width, or an electrode combination. In this manner, the physiological marker may signal the timing of a modification to neurostimulation.

Figure 5:
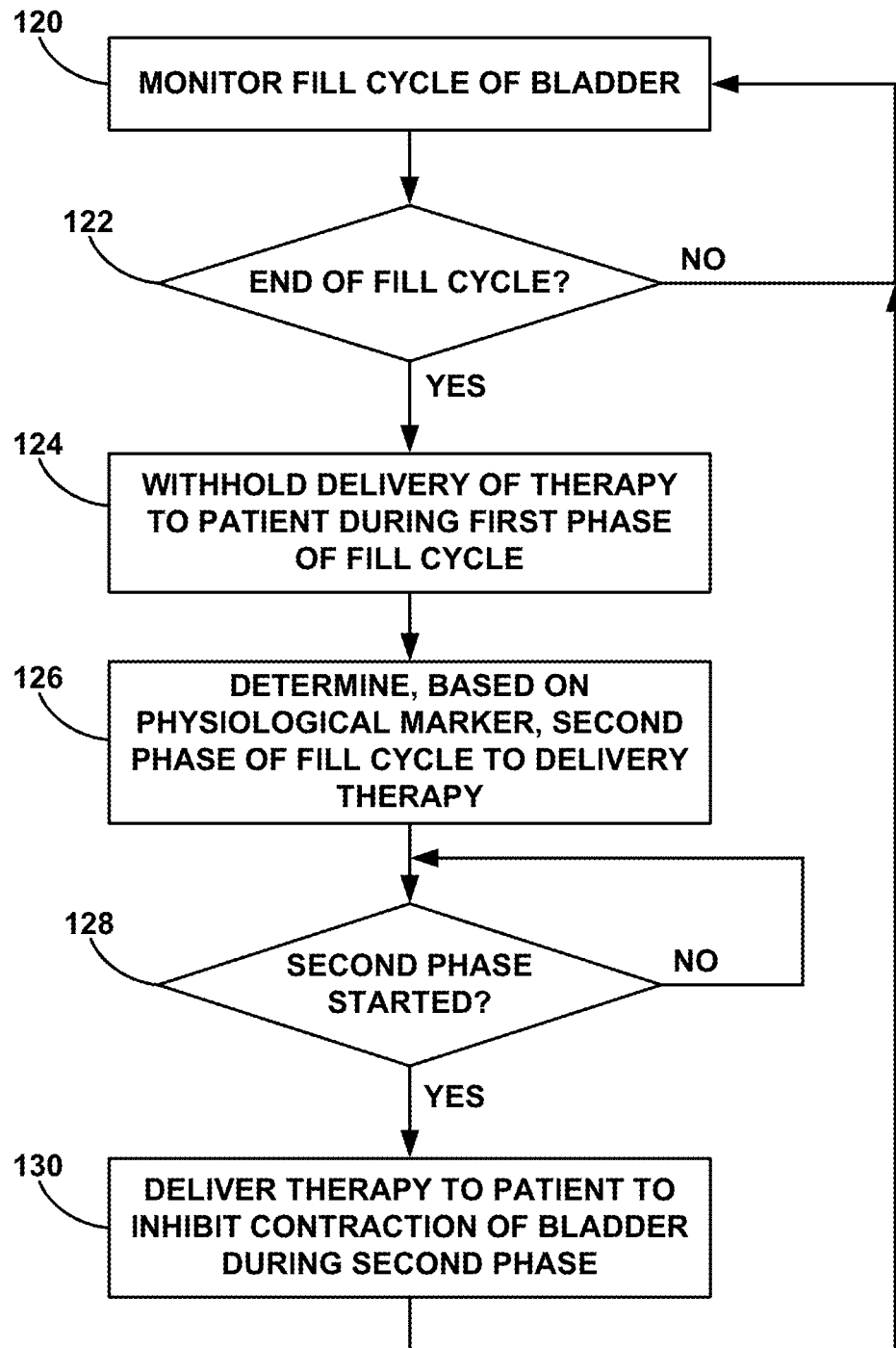
FIG. 5 is a flow diagram that illustrates an example technique for determining phases to withhold and delivery neurostimulation to manage bladder dysfunction.

FIG. 5 is a flow diagram that illustrates an example technique for determining phases to withhold and delivery neurostimulation to manage bladder dysfunction. The technique of FIG. 5 will be described with respect to control module 50 of IMD 16 for purposes of illustration. However, in other examples, control module 72 of IMD 70 or control module 90 of external programmer 24 may perform similar functions or employ a distributive functionality to with other devices (e.g., functionality split between external programmer 24 and IMD 16).

As shown in FIG. 5, control module 50 may monitor the bladder fill cycle of bladder 12 of patient 14 (120). The fill cycle may be defined by the end of a voiding event through to the end of the next voiding event. However, the fill cycle may include the voiding event at the beginning of the cycle in other examples. If control module 50 does not detect a voiding event signaling the end of the fill cycle ("NO" branch of block 122), control module 50 may continue to monitor the fill cycle of the bladder (120). If control module 50 detects the end of the fill cycle ("YES" branch of block 122), control module 50 may determine to withhold delivery of neurostimulation therapy during the first phase of the fill cycle (124). In some examples, the neurostimulation was terminated prior to or during the voiding event, so control module 50 may simply continue not delivering stimulation. However, if IMD 16 is still delivering stimulation at the end of the voiding event, control module 50 may terminate delivery of the neurostimulation and then withhold further delivery of neurostimulation during the first phase.

Based on a physiological marker, such as one or more voiding events, control module 50 may determine a second phase for the fill cycle (126). The second phase is defined for delivery of neurostimulation at an appropriate time prior to a predicted dysfunctional state of bladder 14 (e.g., overactive bladder contractions). The second phase may have a duration determined to provide therapy when the tissue is receptive to the therapy and a starting point prior to the dysfunction in order to reduce or eliminate the dysfunction. If the second phase has not started yet ("NO" branch of block 128), control module 50 may continue to wait until the first phase has ended. If control module 50 determines that the second phase should start ("YES" branch of block 128), control module 50 starts the second phase and delivers neurostimulation therapy to patient 14 in order to inhibit contractions of bladder 12 during the second phase (130).

The neurostimulation therapy delivered during the second phase of the fill cycle may be configured to reduce or eliminate contractions of bladder 12 (e.g., relax the bladder and reduce the likelihood of incontinence). Although only one phase for stimulation is described, control module 50 may determine two or more phases of the fill cycle during which neurostimulation is delivered. Generally, the second phase, and corresponding neurostimulation, at least begins prior to a dysfunctional state that can occur during that bladder fill cycle. However, control module 50 may control therapy delivery module 52 to deliver neurostimulation until the following voiding event. Control module 50 may control therapy delivery module 52 to deliver a different neurostimulation, e.g., with different stimulation parameters than the stimulation delivered during the second phase, just prior to and/or during the next voiding event to promote voiding. The voiding event may also act as a physiological marker for this voiding promoting stimulation.

In other examples, control module 50 may deliver neurostimulation during the first phase of the process of FIG. 5 instead of withholding all neurostimulation delivery. For example, control module 50 may control the IMD to deliver a first neurostimulation therapy (or multiple different therapies) during the first phase and prior to the second phase. Control module 50 may transition from the first neurostimulation therapy of the first phase to the second neurostimulation of the second phase by changing one or more stimulation parameters defining the first neurostimulation therapy to achieve the parameters of the second neurostimulation therapy for the second phase. Control module 50 may change parameters such as at least one of a voltage amplitude, a current amplitude, a pulse frequency, a stimulation waveform frequency, a pulse width, or an electrode combination. In this manner, the physiological marker may signal the timing of a modification to neurostimulation, not just when to start neurostimulation.

Figure 6:
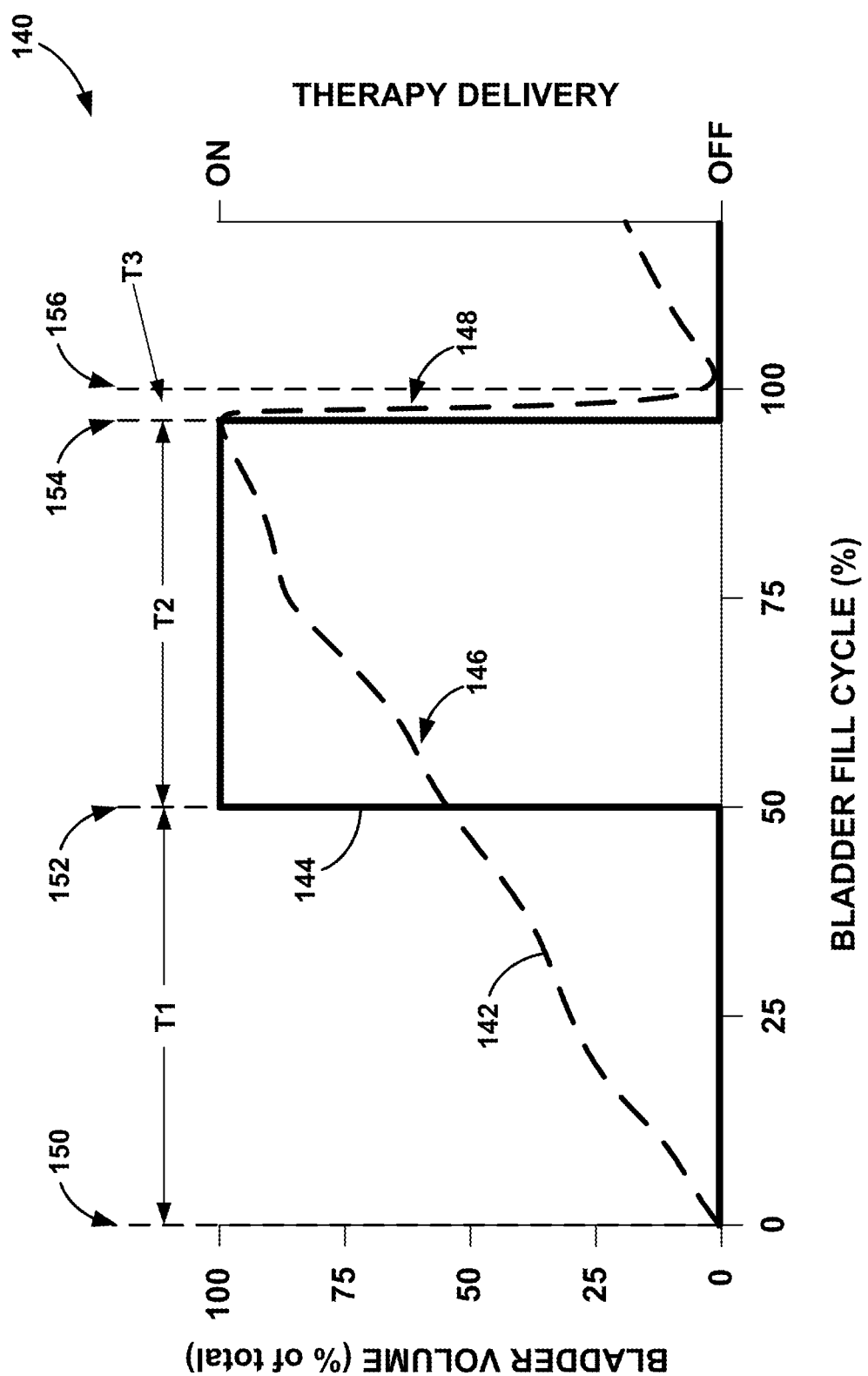
FIG. 6 is an example timing diagram of a bladder fill cycle and delivery of neurostimulation timed to a phase of the bladder fill cycle.

FIG. 6 is an example timing diagram 140 of a bladder fill cycle and delivery of neurostimulation timed to a phase of the bladder fill cycle. As shown in FIG. 6, timing diagram 140 shows the bladder fill cycle with the fill level 142 (e.g., the percentage of full bladder volume) increasing over time during the bladder fill cycle. Portion 146 shows the bladder filling with urine, and portion 148 of fill level 142 shows that bladder 12 is emptying during a voiding event. Stimulation level 144 shows whether stimulation is being delivered or not.

Phase $T_1$ is the first phase of the bladder fill cycle that starts at time 150, and phase $T_2$ is the second phase of the bladder fill cycle that starts at time 152 and runs to time 154. During phase $T_1$, system 10 may withhold stimulation delivery. When the first phase $T_1$ is completed at time 152, system 10 may start the second phase $T_2$ and deliver neurostimulation during this second phase. The timing of the second phase during the fill cycle may be selected to reduce or eliminate dysfunctional states of the bladder as the fill level 142 increases. At the end of phase $T_2$, the patient may need to void at time 154. The beginning of the voiding event during the period $T_3$ is at time 154 and the end of the voiding event is at time 156. Although system 10 terminated delivery of neurostimulation at time 154, neurostimulation may continue during the voiding event in other examples.

Although the second phase $T_2$ is shown as occupying almost the entire second half of the bladder fill cycle, the second phase may occur at other times and with other durations of the fill cycle in other examples. For example, the duration of $T_2$ may only last for a quarter of the fill cycle, and $T_2$ may only occur during the third quartile or the fourth quartile of the bladder fill cycle. In any case, the timing of the first phase and the second phase may be based on a voiding event (e.g., a physiological marker) and historical fill cycles in order to predict when to deliver neurostimulation in order to reduce or eliminate the dysfunctional state (e.g., overactive bladder) during the physiological cycle (e.g., the fill cycle).

FIGS. 7A-10B relate to experimental data and also show conceptual timing of neurostimulation to reduce bladder dysfunction. The experimental data was obtained using a novel sacral neurostimulation (SC S) model in the rat with bilateral bipolar electrode stimulation of the L6S1 roots. With this stimulation, together with published stimulus parameters, we were able to produce bladder areflexia (i.e. complete blockade of bladder-to-bladder reflexes) under conditions of SNS below somatomotor threshold in many animals. These stimulation delivery paradigms were examined to determine whether intermittent application of stimulation timed to certain intervals during the filling portion of the fill cycle (e.g. immediately post-void, timed to mid-cycle or immediately preceding voids) can produce similar effects of increasing bladder capacity shown by continuous stimulation throughout the fill cycle. Battery life may be increased and patient side effects may be decreased by such an approach of intermittent neurostimulation using a timed approach based on voiding events and/or fill cycle levels.

Electrodes were fashioned from 50 micron diameter stainless steel wire with epoxy coating. The electrodes were paired as poles and joined at the binding post of the stimulator terminals. Rostral poles were positioned rostrally on the nerve bilaterally and the leads were then combined and inserted into the output terminal binding post of the FHC Pulsar 6 bp stimulator, and the caudal poles were positioned caudally on the nerve bilaterally and the leads were then combined and inserted into the ground terminal binding post. Parafilm acted to electrically isolate the electrodes. Female Sprague-Dawley rats (250-275 g BW, n=13) were anesthetized with urethane (1.2 g/kg s.c.). Jugular vein catheters were inserted unilaterally for hydration, a transvesical catheter was inserted into a cystotomy in the apex of the bladder dome and ligated in position, and the L6-S1 trunks were isolated as they passed from ventral to dorsal sacrum. Small sheets of Parafilm were inserted between the nerves and the sciatic, inferior iliac vein and other surrounding tissues, isolating the L6-S1 trunks of the spinal cord electrically in that region. Then, two leads were conjoined for co-insertion into the positive pole of the stimulator and placed bilaterally at the rostral aspect of the exposed L6-S1 trunk of the spinal cord. Two additional lead were conjoined for insertion into the negative pole of the stimulation device and placed bilaterally 0.5-1.0 cm caudal to the positive poles. The trunks were covered with mineral oil and the wires were anchored into place on midline tissues using tissue adhesive. The back skin was carefully closed with wound clips. Animals were mounted in Ballman cages to ensure that the bladder catheter was free to move during filling and voiding. A heat lamp was placed nearby to maintain body temperature. The bladder catheters were hooked up to infusion pumps and pressure transducers by 4-way stopcock and infusion was begun for a one hour recovery/accommodation period at a flow rate of 0.1 ml/min. Following controlled and continuous cystometry, the bladder was emptied and single cystometrograms were performed until a stable baseline True Bladder Capacity was established.

Figure 7B:
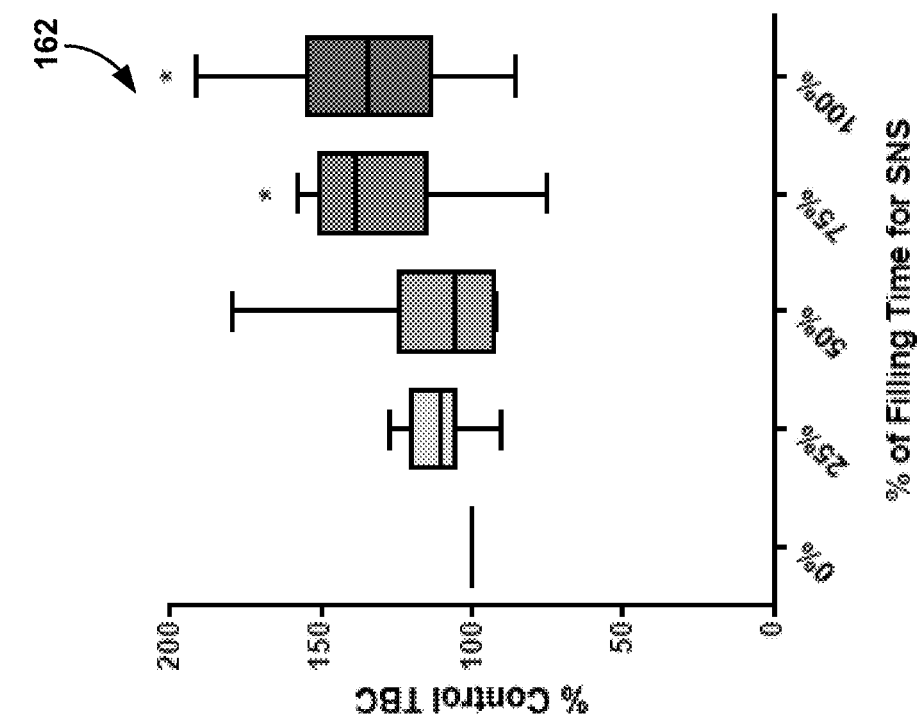
FIGS. 7A and 7B are graphs showing example bladder volumes for neurostimulation delivered during different phases of a bladder fill cycle.
Figure 7A:
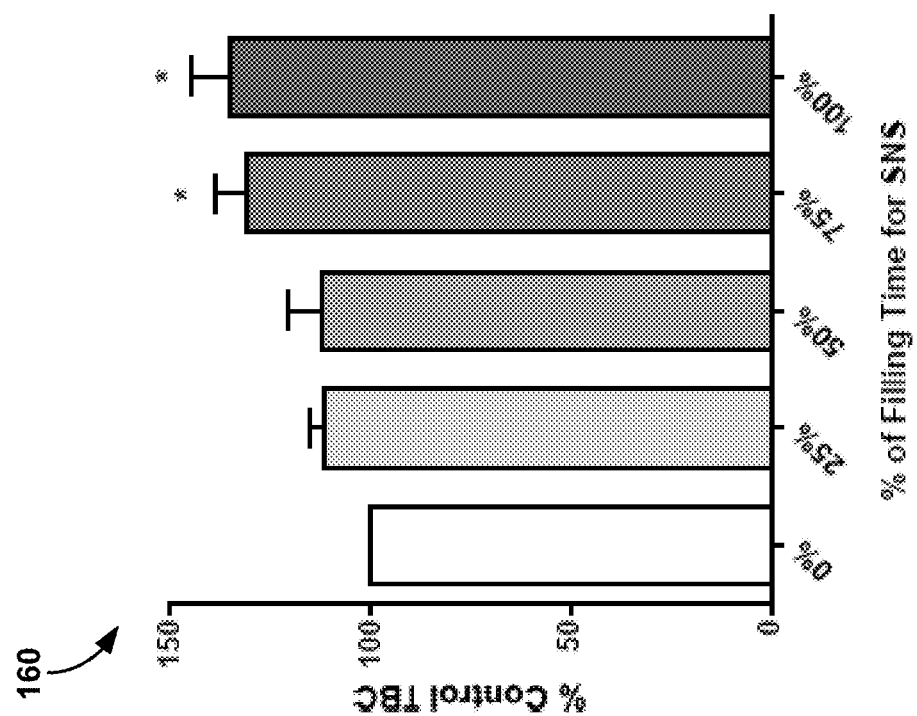
Figure 8B:
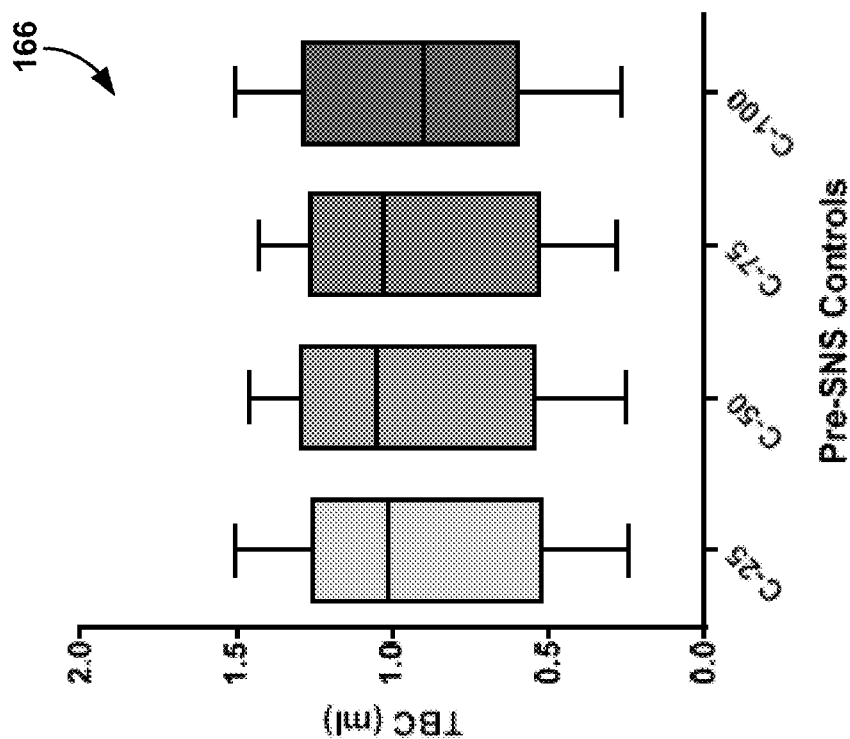
FIGS. 8A and 8B are graphs showing example bladder volumes prior to neurostimulation delivery shown in FIGS. 7A and 7B.
Figure 8A:
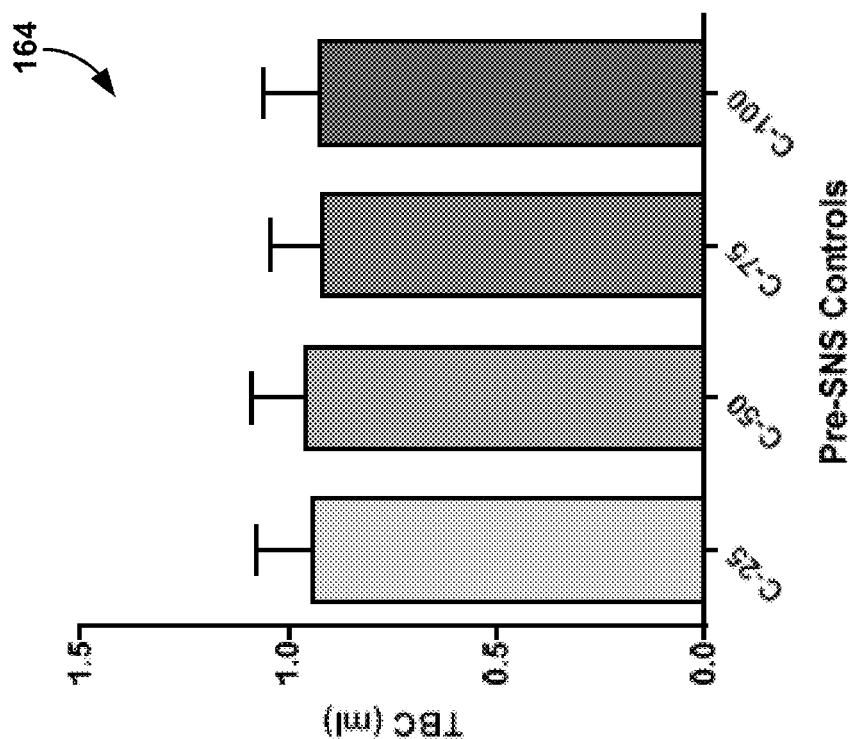

FIGS. 7A and 7B are graphs 160 and 162 showing example bladder volumes for neurostimulation delivered during different phases of a bladder fill cycle for the experimental rats. As shown in graph 160 of FIG. 7A, sacral neurostimulation (SNS) (i.e., a form of neurostimulation delivered to sacral nerves) was delivered at the onset of bladder filling for 25%, 50%, 75%, or 100% of the previous control bladder filling cycle duration (n=10; FIG. 3). There were no significant differences in pre-SNS baseline control bladder capacities as shown in graphs 164 and 166 of FIGS. 8A and 8B, respectfully. Graphs 164 and 166 of FIGS. 8A and 8B show that consecutive SNS applications did not significantly alter return to baseline conditions and that the effects seen with SNS were not a reflection of alterations in baseline control values. In other words, subsequent changes in bladder capacity should be the result of stimulation delivery at the respective time.

Graph 160 of FIG. 7A shows that under conditions of increasing SNS duration, the positive effect of SNS on bladder capacity is maximal when the stimulation was delivered for 75-100% of the fill cycle. Graph 160 may suggest that SNS stimulation should be delivered for at least 75% duration of fill time or that SNS is maximally effective during the final 50% of the filling cycle. Graph 162 shows the variation in samples for each stimulation duration that begins when the fill cycle begins (e.g., upon completion of the previous voiding event). In this manner, SNS durations of both 75% and 100% of control fill times resulted in significantly larger bladder capacities than control.

Figure 9B:
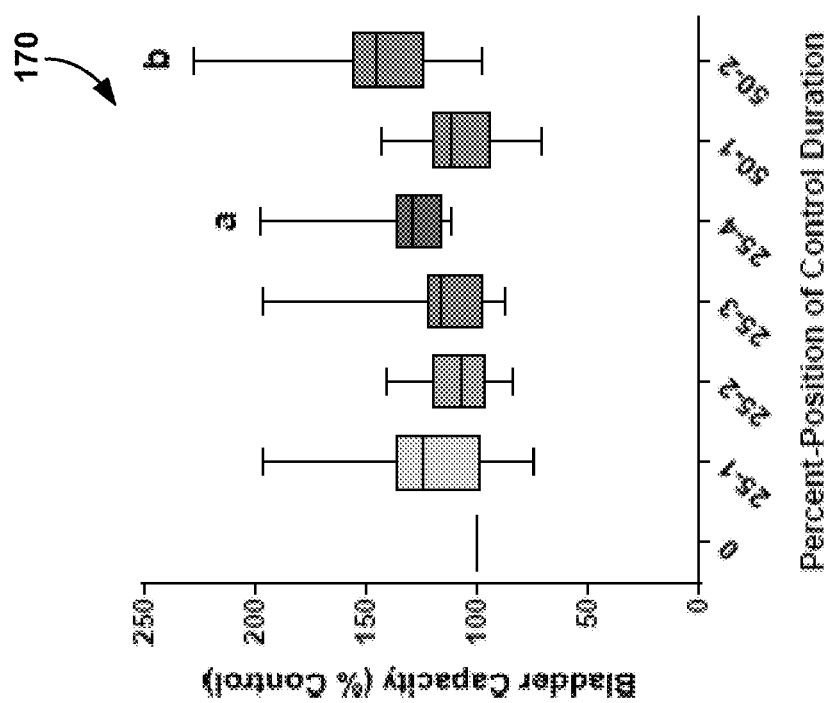
FIGS. 9A and 9B are graphs showing example bladder volumes for neurostimulation delivered during different phases of a bladder fill cycle.
Figure 9A:
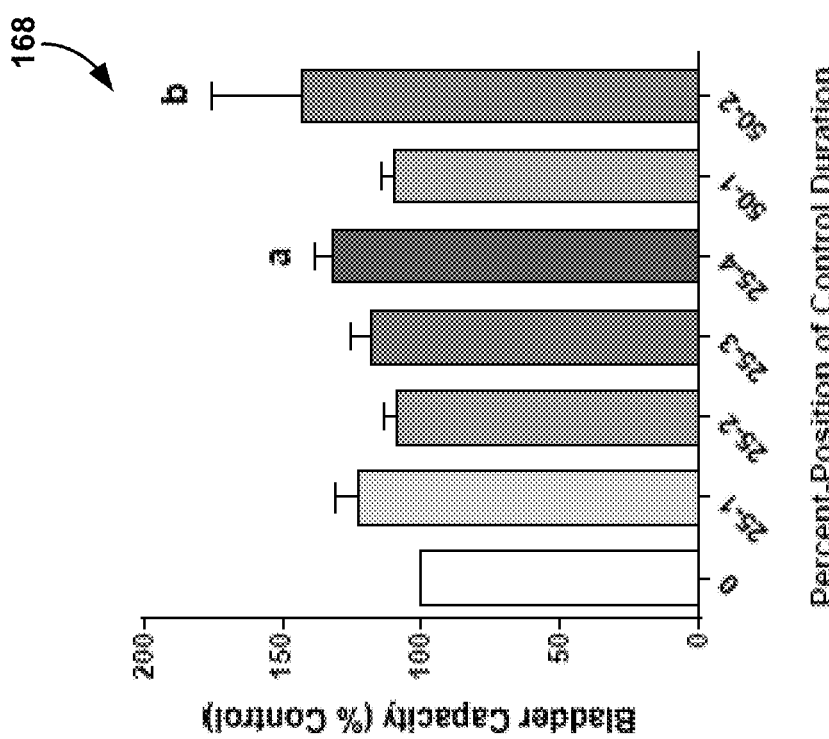

FIGS. 9A and 9B are graphs showing example bladder volumes for neurostimulation delivered during different phases of a bladder fill cycle. Graphs 168 and 170 show the results of an experiment in which SNS delivered to discrete and different regions of the fill cycle was evaluated for any effects on the bladder capacity. SNS was applied during the first 25%, the second 25%, the third 25%, the fourth 25% and the first and second 50% of control fill times in random (all periods randomized in order of application) or pseudo-random order (all of the 25% randomized in order, followed by the 50% s randomized in order). No differences in the randomization approaches were found.

The results of graph 168 indicate that the maximal effect of SNS is achieved when stimulation is applied during the last half or last quarter of the filling cycle. As shown in graph 168, the bladder capacity for the last 75% of the fill cycle (bar 25-4) appears to be the most effective time to deliver stimulation during the fill cycle. The remaining earlier periods of the fill cycle may go unstimulated such that a system can withhold stimulation during the early periods of the fill cycle and still achieve effective treatment for incontinence. Similarly, the last 50% of the fill cycle (bar 50-2) can be an appropriate time for delivery of stimulation with the first 50% remaining unstimulated. Graph 170 shows the variation in bladder capacities due to SNS for all samples in the experiment.

Figure 10B:
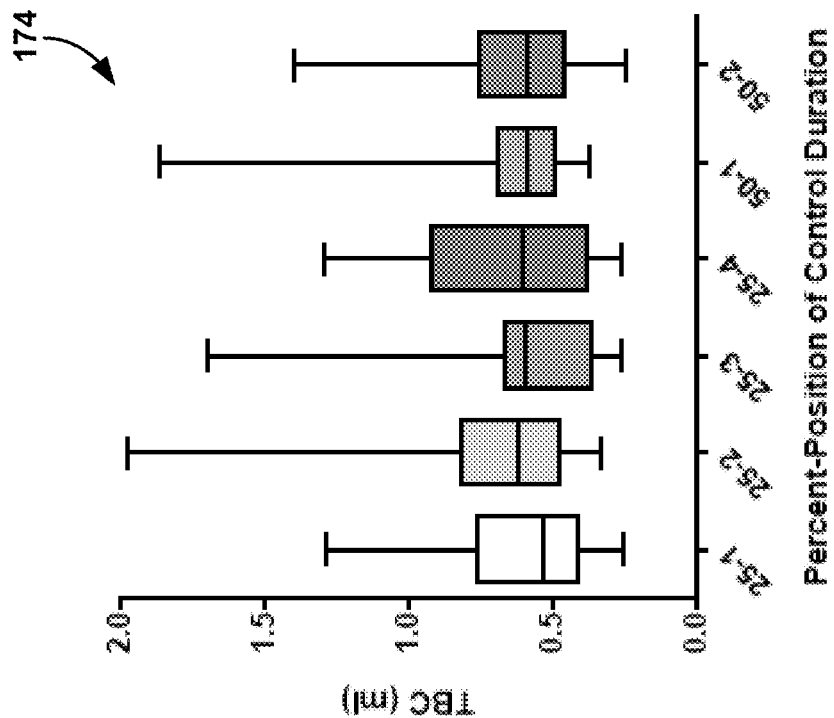
FIGS. 10A and 10B are graphs showing example bladder volumes prior to neurostimulation delivery shown in FIGS. 9A and 9B.
Figure 10A:
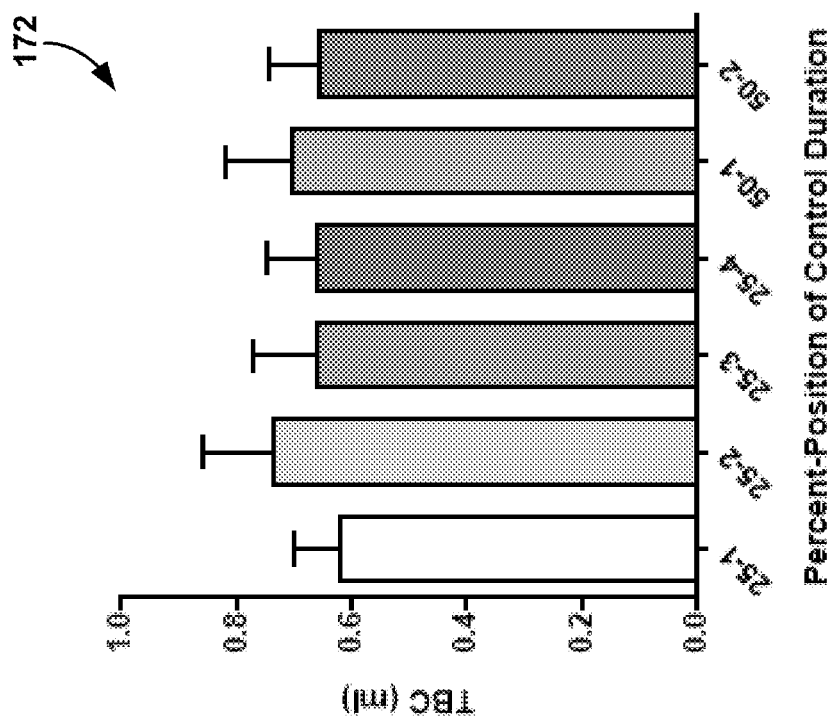

As shown in FIGS. 10A and 10B, graphs 172 and 174 show example bladder volumes prior to neurostimulation delivery as the baseline control bladder capacities prior to each successive SNS application. No statistical significance was detected by Friedman Test. Therefore, consecutive SNS applications did not significantly alter return to baseline conditions and that the effects seen with SNS were not a reflection of alterations in baseline control values. The more effective stimulation phases at the end of the fill cycle appear to be the result of stimulation at those times timed during the fill cycle.

Figure 11:
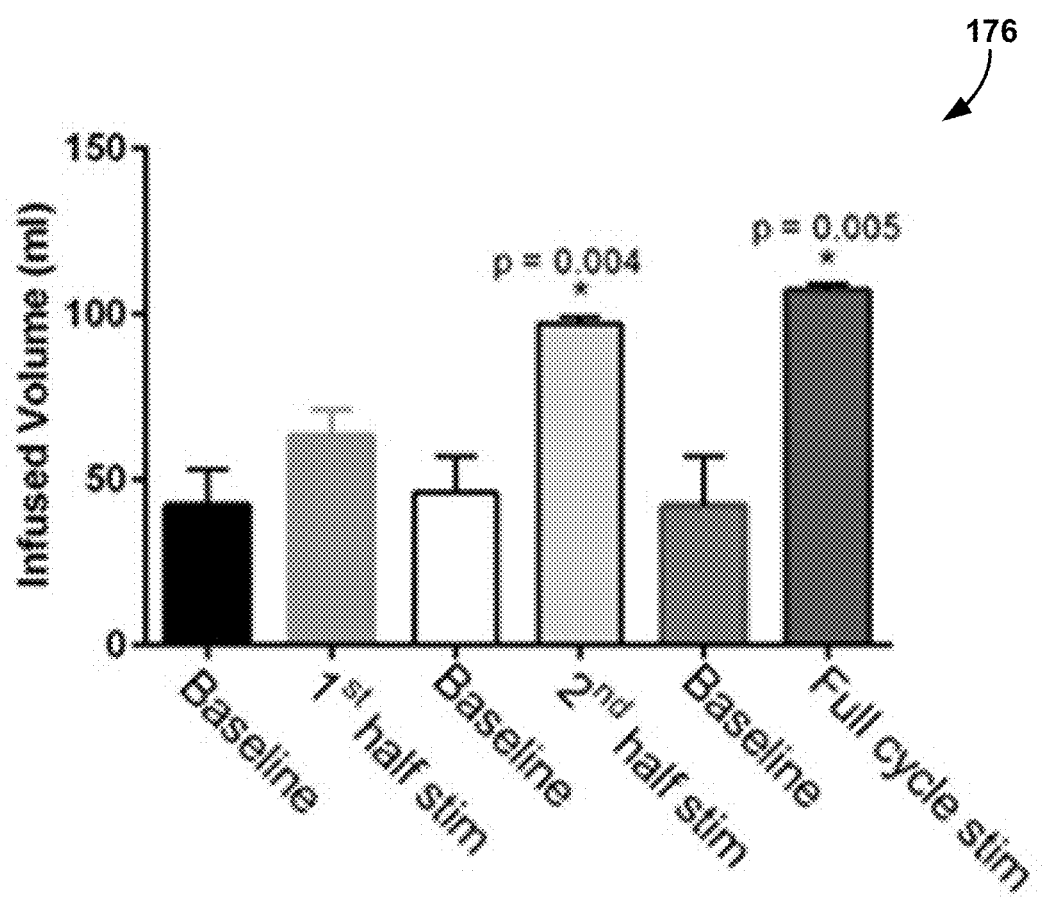
FIG. 11 is a graph showing example bladder volumes changes based on neurostimulation delivered during different phases of a bladder fill cycle.

FIG. 11 is a graph showing example bladder volumes changes based on neurostimulation delivered during different phases of a bladder fill cycle in an experiment involving female sheep. Graph 176 shows the results of an experiment in which SNS delivered to discrete and different regions of the bladder fill cycle was evaluated for any effects on the bladder capacity, or the amount of urine that could be stored by the bladder during a single balder fill cycle. The results of graph 176 were derived from eleven trials with four fully conscious, female sheep implanted with an IMD. In each trial, fluid was added to the bladder at a rate of 15 milliliters (mL) until the animal voided the contents of the bladder. The total amount of fluid that had been added prior to voiding was recorded for each condition. Three baseline bladder fill cycles were conducted to establish a mean bladder filling time, at which time subsequent and separate bladder fill cycles were performed in which neuromodulation was delivered for the first half of the bladder fill cycle, the second half of the bladder fill cycle, and the full period of the bladder fill cycle, respectively. Each bar in graph 176 is shown with respective error parts.

As shown in graph 176, baseline bladder fill cycles resulted in approximately 40 mL of volume held prior to voiding when no neurostimulation was delivered during the bladder cycle. When neurostimulation was delivered during only the first half of the bladder fill cycle (i.e., no neurostimulation was delivered during the second half of the bladder fill cycle), the fill volume increased to approximately 70 mL. However, this volume increase was not statistically significant compared to the baseline. When neurostimulation was delivered only during the second half of the bladder fill cycle (i.e., no neurostimulation during the first half), the total fill volume was increased a statistically significant amount over the baseline volume to approximately 100 mL. Similar increases to bladder volume over baseline were observed during neurostimulation delivery during the entire, or full, bladder fill cycle. Therefore, these results indicate that neurostimulation can be delivered during the second half, or a second phase, of the bladder fill cycle instead of the first half, or first phase of the bladder fill cycle. Withholding stimulation during the first phase to avoid continual stimulation delivery may increase long term efficacy and prevent accommodation and/or muscle fatigue while maintaining effective therapy.

Figure 12A:
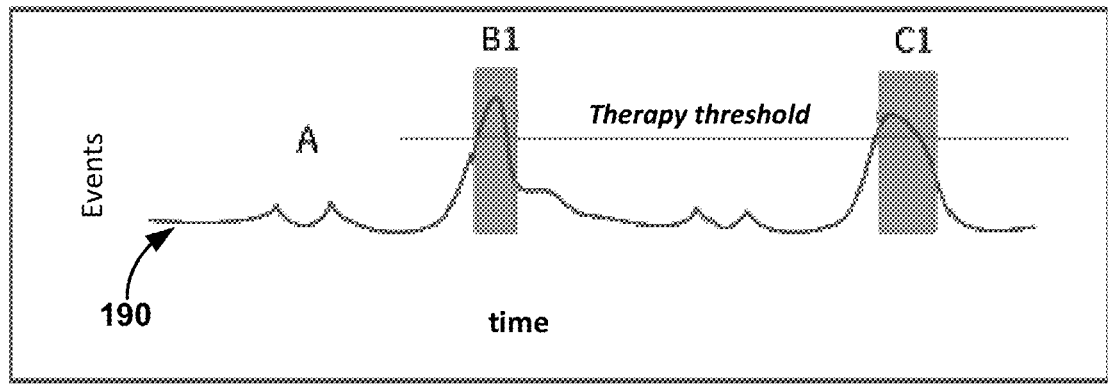
FIGS. 12A and 12B are graphs showing example physiological events during a physiological cycle and predictive delivery of neurostimulation to avoid a dysfunctional state of the physiological cycle.
Figure 12B:
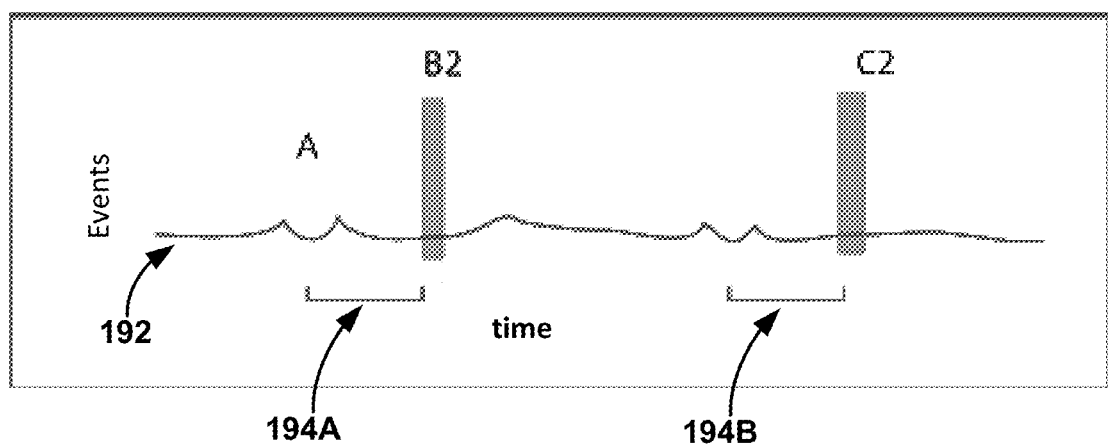

FIGS. 12A and 12B are graphs showing example physiological events during a physiological cycle and predictive delivery of neurostimulation to avoid a dysfunctional state of the physiological cycle. Instead of electrical and pharmaceutical based neuromodulation therapies being delivered continuously, these therapies may be delivered in response to detection of a dysfunctional state. As shown in FIG. 12A, event line 190 may show bladder contractions, as one example, during two bladder fill cycles wherein the bladder contractions occur during time periods B1 and C1. The bladder contractions exceed a therapy threshold to arrive at a dysfunctional state (e.g., overactive bladder that may result in incontinence) that may benefit from stimulation during periods B1 and C1. However, this stimulation is too late in time to prevent the dysfunctional state.

Instead of waiting to detect the dysfunction before delivering stimulation, detection of a physiological marker A prior to the dysfunction may allow a system to predict when stimulation should be delivered prior to the dysfunction occurring. Marker A may be a detectable physiological event, such as a voiding event, a bladder fill level, or minor detrusor contractions for the case of incontinence. As shown in FIG. 12B, event line 192 also includes marker A. However, upon detecting the physiological marker A, the system may track a first phase 194A during which stimulation therapy is withheld from the patient. Upon expiration of the first phase 194A, the system may deliver neurostimulation during the second phase B2 in anticipation of the dysfunctional state. Neurostimulation during C2 of the next fill cycle may have a similar effect. In this manner, the system may refrain from delivering stimulation when it is unnecessary for therapy and possibly prevent the dysfunctional state from occurring by pre-treating the organ or related tissue. In addition, preemptively delivering stimulation may reduce the time required for stimulation delivery because the stimulation does not need to counteract the dysfunction that has already occurred. Timing delivery of neurostimulation to one or more physiological markers, instead of waiting to detect a dysfunction, may improve efficacy, reduce side effects from shorting stimulation durations, reduce accommodation, and improve battery life or drug fill intervals.

In the example of urinary bladder applications, urinary physiology is governed by phases of bladder filling and urine storage (e.g., a filling phase) coupled with phases of bladder contractions associated with urine release (e.g., a voiding phase). Additionally, these two broad phases can also be subdivided into at least three discrete subphases, as the voiding phase is composed of void initiation, void maintenance and void termination phases. Filling, in turn, is composed of at least three subphases including fill initiation, fill maintenance, and fill termination. Each sub phase is associated with specific neural sensory inputs and motor outputs that establish a complete functional network. By timing neurostimulation onto these specific subphases of function, the system and method may achieve an improved network function according to relative physiological and temporal signals within and associated with these subphases. Similar functions for other organ systems can also be described according to physiological markers and temporal relationships with those markers with phases and subphases of activity or states.

In some examples, one or more non-voiding (e.g. no urination expulsion) bladder contractions associated with phases of bladder filling and non-voiding bladder contractions may be used as physiological markers indicative of sensations of urgency. Three types of non-voiding bladder contractions may include type I, type II, and type III contractions. Type I contractions include base-to-dome in propagation, small magnitude, contractions that typically lead to bladder volume accommodation. Type I contractions are associated with normal filling and accommodation of the bladder (increases in volume) as the bladder fills with urine. Type II contractions are dome-to-base in propagation, larger magnitude, reverse contractions that are observed during high bladder volumes and pressures or during certain types of bladder irritation (e.g. disease state). Type II contractions (or dysfunctions of these) are associated with fullness (urge) and potentially bladder or pelvic pain. The presence of Type II contractions at lower bladder volumes may be associated with a variety of idiopathic urge frequency and/or urge incontinence conditions. It also possible that bladder pain syndrome could include an increase in Type II contractions. Type III contractions are similar to Type I contractions in originating from base-to-dome, but Type III contractions invade into the dome and return towards base. These contractions are larger in magnitude and have been primarily observed in older rats, for example. These contractions (or dysfunctions of these) might be associated with the increase in urge and frequency symptoms common in older patients.

These types of bladder contractions could be identified using either chronic or acute measurement techniques. Acutely, the contractions could be measured in-office via techniques with multi-channel pressure catheters, or a variety of imaging techniques from endoscopic video recording, ultrasound and/or functional MM. Filling cystometry could be used to help quickly identify different types of contractions present in a patient for diagnostic purposes as well as therapy selection for an individual patient. Chronically, techniques for recording non-voiding contractions could include focal EMG, chemical sensors, or local pressure or mechanical sensors within the bladder or outside the bladder wall. These long-term recording methods could help identify different contraction types and changes in frequency or amplitude after a therapy has been applied.

Distinguishing these different types of bladder contractions (especially Types II & III) by various methods could allow for differential diagnosis and subsequent efficacious respective therapies based upon these specific dysfunctions. For example, detection of Type II and/or Type III contractions would also serve as a physiological marker for idiopathic overactive bladder and potentially differentiate bladder specific (e.g. bladder muscle or neural input) disease from generalized disorders (e.g. anxiety, depression) that can negatively impact urinary behavior. In this manner the system may use the different contractions as a marker to time subsequent therapy and reduce dysfunctional events such as overactive bladder.

Specific urinary incontinence features may include using patient sensation of urination, patient sensation of emptiness, and/or of pain or bladder fullness as a signal relating to bladder filling phase. Patient reports (e.g., user input) of urination or reports of urine leakage can also be used to detect voiding phase or abnormal voiding, respectively. This user input includes one or more signals from which physiological markers can be identified. In this manner, leakage, or a leakage event, is different from a voiding event. In the case of the bladder, leakage refers to an amount of urine that exits the bladder that is less than a full emptying of the bladder, whereas full emptying (e.g., emptying until the bladder is empty or substantially empty where urine no longer exits the bladder) is considered a voiding event or void event. For example, leakage may refer to a small amount of urine that exits the bladder and then stops such that the remainder of urine is still retained within the bladder. Leakage events may result in abnormal voiding and an unstable or abnormal fill cycle. In some examples, the system may ignore identified leakage events when determining a voiding event that stops and starts a fill cycle. In other examples, the system may characterize the fill cycle as an unstable fill cycle in response to identifying a leakage event and treat the fill cycle differently than a fill cycle that is normal and without any identified leakage events.

Patient actuation (e.g., user input) of specific sensations or events recorded to a device can be used to indicate specific phases within filling or voiding. Therapy timing systems can be linked to the patient-indicated signals so that therapy delivery can be partitioned and delivered appropriately relative to the indicated signals. In addition, automated and objective sensing of bladder physiological markers can be utilized to link with urinary phase, such as pressure signals and large rapid changes in bladder pressure that indicate urination events or linked with urge (i.e., a patient sensation of a need to void). Bladder movement (detected by accelerometers, piezoelectric sensors, or similar sensors) can be used as physiological markers of voiding or instability of bladder filling. Pressure spectra of the bladder can be used to identify dysfunction of normal filling. The system can utilize bladder or urethral pressure, patterns or pressure spectra, or external bladder pressures detected near the bladder. Other physiological signals include nerve activity, urine flow, and EMG activities from the internal or external urethral sphincter or detrusor muscle.

A variety of physiological markers are described herein and can be used to determine the start, end, and/or progression point within a physiological cycle. Physiological markers may be indicated by an identified event such as voiding, leaking, muscle activation, or other events related to urine or fecal voiding. These events may be detected automatically by implanted or external sensors. For example, a wetness sensor may detect voiding or leakage external of the patient, a pressure sensor may detect bladder pressure and/or sphincter pressure via an implanted or external position, or electrodes may generate an electrogram indicative of pelvic floor muscle activity. In some examples, external and/or implanted electrodes may generate an electroencephalogram (EEG) from which a physiological marker indicative of pelvic muscle contraction related to one or more events of the physiological cycle. Other physiological markers may be derived from external monitoring of patient behavior, patient activity, or even patient location. For example, individual events or activities related to a bladder fill cycle (e.g., pacing, fidgeting, swaying, or other activities indicative of impending voiding) may be used to identify voiding or impending voiding. As another example, a pattern of events or activities may be used to identify a point in the physiological cycle, such as a period of non-motion immediately following pacing or fidgeting, which may indicate that voiding is occurring during the non-motion period, or detection of increasing use of legs during pacing, contraction of buttocks or other muscle activity, which may indicate that the bladder fill cycle is approaching the end. In some examples, a sensor (e.g., proximity sensor and/or location sensor) may indicate when the patient is within an area identified as a restroom where the patient typically voids and interpret the presence within this area as the patient is voiding. The programmer or IMD may directly detect these areas or locations (e.g., using global position system (GPS) sensors and/or one or more proximity sensors) or receive indications of the patient location from another sensor or device (e.g., from a smartphone or dedicated presence-sensitive sensor such as a pressure sensor on the seat of a toilet, trigger on the toilet flushing mechanism, or any other such sensor). In other examples, a physiological marker may be detected based on input from a patient such as an indication that the patient has voided, needs to void, or is requesting additional or alternative therapy in order to prevent a voiding event.

In addition, a single physiological marker may be identified from two or more signals. These signals may be synchronized in time such that the physiological marker is identified when an aspect of each synchronized signal matches a predetermined value or exceeds a predetermined threshold. For example, the physiological marker for a voiding event may be the detection of bladder contraction and wetness from a wetness sensor. As another example, a voiding event may be detected when the patient is detected to be within a restroom and the patient is not moving for at least a certain period of time that indicates the patient has voided. In this manner, the system may detect a physiological marker by analyzing two or more signals.

Phases of bladder function can be detected and therapy delivery can be linked to these critical phases. If the normal phases of function are not present, or dysfunctional events are detected, then therapies can be delivered relative to a desired normal function. Timing can be used to appropriately delay stimulation relative to major physiological events or identifiable bladder stages. For example, the system can detect voiding or unstable detrusor contractions and link such events to neurostimulation delivery or withholding. Voiding, whether recorded by patient actuation or physiological recording, can be used by a system to initiate a timer that allows the therapy to be discontinued, or withheld, for a duration of a phase following this phase and then therapy can be reinitiated following this phase. Initiation of therapies can therefore be applied in shorter durations linked to voiding events, with therapy delivery being needed in the latter phase of filling instead of the early phase after a void event, for example.

It should be noted that system 10, and the techniques described herein, may not be limited to treatment or monitoring of a human patient. In alternative examples, system 10 may be implemented in non-human patients, e.g., primates, canines, equines, pigs, and felines. These other animals may undergo clinical or research therapies that my benefit from the subject matter of this disclosure.

Various examples are described herein, such as the following examples. Example 1: a method comprising monitoring, by one or more processors, a fill cycle of a bladder of a patient, the fill cycle starting after completion of a first voiding event and ending at the completion of a second voiding event, determining, by the one or more processors and based on one or more physiological markers associated with the fill cycle, a first phase including and following the start of the fill cycle and a second phase of the fill cycle immediately following the first phase, wherein the second phase is determined to include delivery of neurostimulation therapy configured to inhibit contraction of a bladder of the patient, and controlling, by the one or more processors, a medical device to deliver the neurostimulation therapy to the patient during the second phase of the fill cycle.

Example 2: the method of example 1, further comprising controlling, by the one or more processors, the medical device to withhold delivery of all neurostimulation therapy to the patient for the first phase of the fill cycle.

Example 3: the method of example 1, wherein the neurostimulation therapy is a first neurostimulation therapy, and wherein the method further comprises controlling the medical device to deliver a second neurostimulation therapy different than the first neurostimulation during the first phase.

Example 4: the method of example 3, further comprising transitioning from the second neurostimulation therapy of the first phase to the first neurostimulation of the second phase by changing, for the second neurostimulation therapy, at least one of a voltage amplitude, a current amplitude, a pulse frequency, a stimulation waveform frequency, a pulse width, or an electrode combination.

Example 5: the method of any of examples 1 through 4, wherein determining the second phase of the fill cycle comprises tracking a time period from the first voiding event, and comparing the time period to a fill time threshold, and responsive to the time period exceeding the fill time threshold, initiating the second phase of the fill cycle.

Example 6: the method of example 5, further comprising estimating the fill time threshold based on respective durations of a plurality of previous fill cycles of the patient.

Example 7: the method of example 6, wherein calculating the fill time threshold comprises calculating an average of the respective durations of the plurality of previous fill cycles, determining an estimated second phase duration based on the average, and determining the fill time threshold as an initiation point for the second phase based on the average of the respective durations of the plurality of previous fill cycles.

Example 8: the method of any of examples 1 through 7, wherein the one or more physiological markers comprises a fill level of the bladder, and wherein determining the second phase of the fill cycle comprises detecting a magnitude of the fill level, comparing the magnitude of the fill level to a threshold, and, responsive to the magnitude of the fill level exceeding the threshold, initiating the second phase of the fill cycle.

Example 9: the method of example 8, wherein detecting the magnitude of the fill level comprises detecting a pressure level of the bladder.

Example 10: the method of any of examples 8 and 9, wherein detecting the magnitude of the fill level comprises detecting an impedance level of the bladder.

Example 11: the method of any of examples 1 through 10, wherein the second phase occurs during a third quartile of the fill cycle instead of a first quartile or a second quartile of the fill cycle.

Example 12: the method of any of examples 1 through 11, wherein the second phase occurs during a fourth quartile of the fill cycle instead of a first quartile, a second quartile, or a third quartile of the fill cycle.

Example 13: the method of any of examples 1 through 12, wherein the first phase occurs during a first half of the fill cycle and the second phase occurs during a second half of the fill cycle instead of the first half.

Example 14: the method of any of examples 1 through 13, wherein monitoring the fill cycle comprises detecting the first voiding event and the second voiding event.

Example 15: the method of example 14, wherein detecting the first voiding event and the second voiding event comprises receiving an indication of a user input representative of an occurrence of at least one of the first voiding event and the second voiding event.

Example 16: the method of example 14, wherein detecting the first voiding event and the second voiding event comprises at least one of detecting at least one of a pressure of the bladder, a flow of urine from the bladder, a wetness of an article external of the patient, an electromyogram (EMG) signal, a nerve recording, a posture change, a physical location of the patient within a structure, or a toilet use event.

Example 17: the method of any of examples 1 through 16, further comprising detecting at least one of the first voiding event or the second voiding event and, responsive to the detection, controlling the medical device to terminate delivery of the neurostimulation therapy.

Example 18: the method of any of examples 1 through 17, wherein the neurostimulation therapy is a first neurostimulation therapy, and wherein the method further comprising controlling the medical device to deliver a second neurostimulation therapy during the at least one of the first voiding event or the second voiding event, the second neurostimulation therapy configured to promote bladder voiding.

Example 19: a system comprising one or more processors configured to monitor a fill cycle of a bladder of a patient, the fill cycle starting after completion of a first voiding event and ending at the completion of a second voiding event, determine, based on one or more physiological markers associated with the fill cycle, a first phase including and following the start of the fill cycle and a second phase of the fill cycle immediately following the first phase, wherein the second phase is determined to include delivery of neurostimulation therapy configured to inhibit contraction of a bladder of the patient, and control a medical device to deliver the neurostimulation therapy to the patient during the second phase of the fill cycle.

Example 20: the system of example 19, wherein the one or more processors are configured to control the medical device to withhold delivery of all neurostimulation therapy to the patient for the first phase of the fill cycle.

Example 21: the system of example 19, wherein the neurostimulation therapy is a first neurostimulation therapy, and wherein the one or more processors are configured to control the medical device to deliver a second neurostimulation therapy different than the first neurostimulation during the first phase.

Example 22: the system of example 21, wherein the one or more processors are configured to transition from the second neurostimulation therapy of the first phase to the first neurostimulation of the second phase by changing, for the second neurostimulation therapy, at least one of a voltage amplitude, a current amplitude, a pulse frequency, a stimulation waveform frequency, a pulse width, or an electrode combination.

Example 23: the system of examples 19 through 22, wherein the one or more processors are configured to determine the second phase of the fill cycle by tracking a time period from the first voiding event, comparing the time period to a fill time threshold, and responsive to the time period exceeding the fill time threshold, initiating the second phase of the fill cycle.

Example 24: the system of example 23, wherein the one or more processors are configured to estimate the fill time threshold based on respective durations of a plurality of previous fill cycles of the patient.

Example 25: the system of example 24, wherein the one or more processors are configured to calculate the fill time threshold by calculating an average of the respective durations of the plurality of previous fill cycles, determining an estimated second phase duration based on the average, and determining the fill time threshold as an initiation point for the second phase based on the average of the respective durations of the plurality of previous fill cycles.

Example 26: the system of any of examples 19 through 25, wherein the one or more physiological markers comprises a fill level of the bladder, and wherein the one or more processors are configured to determine the second phase of the fill cycle by detecting a magnitude of the fill level, comparing the magnitude of the fill level to a threshold, and, responsive to the magnitude of the fill level exceeding the threshold, initiating the second phase of the fill cycle.

Example 27: the system of example 26, wherein the one or more processors are configured to detect the magnitude of the fill level by detecting a pressure level of the bladder.

Example 28: the system of example 26, wherein the one or more processors are configured to detect the magnitude of the fill level by detecting an impedance level of the bladder.

Example 29: the system of any of examples 19 through 28, wherein the second phase occurs during a third quartile of the fill cycle instead of a first quartile or a second quartile of the fill cycle.

Example 30: the system of any of examples 19 through 28, wherein the second phase occurs during a fourth quartile of the fill cycle instead of a first quartile, a second quartile, or a third quartile of the fill cycle.

Example 31: the system of any of examples 19 through 28, wherein the first phase occurs during a first half of the fill cycle and the second phase occurs during a second half of the fill cycle instead of the first half.

Example 32: the system of any of examples 19 through 31, wherein monitoring the fill cycle comprises detecting the first voiding event and the second voiding event.

Example 33: the system of example 32, wherein the one or more processors are configured to detect the first voiding event and the second voiding event by receiving an indication of a user input representative of an occurrence of at least one of the first voiding event and the second voiding event.

Example 34: the system of example 32, wherein the one or more processors are configured to detect the first voiding event and the second voiding event by at least one of detecting at least one of a pressure of the bladder, a flow of urine from the bladder, a wetness of an article external to the patient, an electromyogram (EMG) signal, a nerve recording, a posture change, a physical location of the patient within a structure, or a toilet use event.

Example 35: the system of any of examples 19 through 34, wherein the one or more processors are configured to detect at least one of the first voiding event or the second voiding event, and responsive to the detection, control the medical device to terminate delivery of the neurostimulation therapy.

Example 36: the system of any of examples 19 through 35, wherein the neurostimulation therapy is a first neurostimulation therapy, and wherein the one or more processors are configured to control the medical device to deliver a second neurostimulation therapy during the at least one of the first voiding event or the second voiding event, the second neurostimulation therapy configured to promote bladder voiding.

Example 37: the system of any of examples 19 through 36, further comprising the medical device, wherein the medical device comprises a therapy delivery module configured to deliver the neurostimulation therapy to the patient.

Example 38: the system of example 31, wherein the therapy delivery module comprises at least one of an electrical stimulation generator or a drug pump.

Example 39: the system of example 31, further comprising one or more implantable medical leads coupled to the medical device, wherein the one or more implantable medical leads comprise one or more respective electrodes configured to transmit neurostimulation to the patient from the therapy delivery module.

Example 40: the system of any of examples 19 through 39, wherein the medical device comprises the one or more processors.

Example 41: a non-transitory computer-readable medium comprising instructions that, when executed, cause one or more processors to monitor a fill cycle of a bladder of a patient, the fill cycle starting after completion of a first voiding event and ending at the completion of a second voiding event, determine, based on one or more physiological markers associated with the fill cycle, a first phase including and following the start of the fill cycle and a second phase of the fill cycle immediately following the first phase, wherein the second phase is determined to include delivery of neurostimulation therapy configured to inhibit contraction of a bladder of the patient, and control a medical device to deliver the neurostimulation therapy to the patient during the second phase of the fill cycle.

Example 42: a system comprising means for monitoring a fill cycle of a bladder of a patient, the fill cycle starting after completion of a first voiding event and ending at the completion of a second voiding event, means for determining, based on one or more physiological markers associated with the fill cycle, a first phase including and following the start of the fill cycle and a second phase of the fill cycle immediately following the first phase, wherein the second phase is determined to include delivery of neurostimulation therapy configured to inhibit contraction of a bladder of the patient, and means for controlling a medical device to deliver the neurostimulation therapy to the patient during the second phase of the fill cycle.

Example 43: the system of example 42, further comprising means for detecting the first voiding event and the second voiding event.

Example 44: the system of example 35, further comprising means for delivering the neurostimulation therapy to the patient.

Example 45: a method comprising detecting, by one or more processors, a physiological marker that occurs prior in time to a dysfunctional phase of a physiological cycle, wherein a dysfunctional state of the physiological cycle occurs during the dysfunctional phase without treatment, responsive to detecting the physiological marker, initiating, by the one or more processors, a first phase of the physiological cycle having a duration of time, withholding, by the one or more processors, delivery of neurostimulation therapy for the duration of time of the first phase, and responsive to the first phase elapsing, controlling, by the one or more processors, a therapy delivery module to deliver neurostimulation therapy during a second phase that begins prior to the dysfunctional phase, wherein the neurostimulation therapy is configured to treat the dysfunctional state.

Example 46: the method of example 45, wherein the second phase at least partially overlaps with the dysfunctional phase.

Example 47: the method of any of examples 45 and 46, wherein the second phase ends prior to the dysfunctional phase, and wherein the method comprises, responsive to the second phase ending, terminating delivery of the neurostimulation therapy.

Example 48: the method of any of examples 45 through 47, wherein delivery of the neurostimulation therapy during the second phase of the physiological cycle one of reduces or eliminates the dysfunctional state of the physiological cycle.

Example 49: the method of example 48, wherein the physiological cycle is a first physiological cycle, and wherein delivery of the neurostimulation therapy during the first physiological cycle reduces or eliminates the dysfunctional state of a second physiological cycle subsequent to the first physiological cycle without delivery of the neurostimulation therapy during the second physiological cycle.

Example 50: the method of any of examples 45 through 49, wherein the dysfunctional state comprises a bladder dysfunction.

Example 51: the method of example 50, wherein the physiological marker comprises a fill level of the bladder.

Example 52: the method of example 50, wherein the physiological marker comprises a detrusor contraction during the first phase of the physiological cycle.

Example 53: the method of any of examples 45 through 52, wherein the dysfunctional state comprises a colon dysfunction.

Example 54: the method of any of examples 45 through 53, wherein the neurostimulation therapy comprises at least one of electrical stimulation or drug therapy.

Example 55: a system comprising one or more processors configured to perform the method of any of examples 45 through 54.

Example 56: an implantable medical device configured to perform the method of any of claims 45 through 54, the implantable medical device comprising a therapy delivery module configured to deliver the neurostimulation to the patient via one or more medical leads.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. For example, any module described herein may include electrical circuitry configured to perform the features attributed to that particular module, such as fixed function processing circuitry, programmable processing circuitry, or combinations thereof.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method comprising:
   monitoring, by processing circuitry, one or more physiological markers associated with fill cycles of a bladder of a patient;
   withholding, by the processing circuitry and based on the monitoring of the one or more physiological markers, neurostimulation therapy delivery to the patient during a first fill cycle;
   controlling, by the processing circuitry, a medical device to deliver the neurostimulation therapy to the patient during the first fill cycle and subsequent to withholding the neurostimulation therapy delivery during the first fill cycle, the neurostimulation therapy configured to inhibit contraction of the bladder of the patient.

2. The method of claim 1, wherein withholding the neurostimulation therapy delivery comprises:
   determining, based on monitoring the one or more physiological markers, an end of an initial fill cycle; and
   responsive to determining the end of the initial fill cycle, withholding the neurostimulation therapy delivery during the first fill cycle that immediately follows the initial fill cycle.

3. The method of claim 2, wherein determining the end of the initial fill cycle comprises detecting a voiding event of the patient.

4. The method of claim 1, further comprising:
   determining, based on monitoring the one or more physiological markers, an end of the first fill cycle;
   responsive to determining the end of the first fill cycle, withholding the neurostimulation therapy delivery during a second fill cycle that immediately follows the first fill cycle; and
   controlling the medical device to deliver the neurostimulation therapy to the patient during the second fill cycle and subsequent to withholding the neurostimulation therapy delivery during the second fill cycle.

5. The method of claim 1, wherein withholding the neurostimulation therapy delivery comprises withholding delivery of all neurostimulation therapy to the patient.

6. The method of claim 1, wherein controlling the medical device to deliver the neurostimulation therapy comprises determining to deliver the neurostimulation therapy after withholding the neurostimulation therapy by at least:
   tracking a time period from a voiding event associated with an initial fill cycle prior to the first fill cycle;
   comparing the time period to a fill time threshold; and
   responsive to the time period exceeding the fill time threshold, controlling the medical device to deliver the neurostimulation therapy during the first fill cycle and subsequent to withholding the neurostimulation therapy during the first fill cycle.

7. The method of claim 6, further comprising predicting the fill time threshold based on respective durations of a plurality of previous fill cycles of the patient.

8. The method of claim 1, wherein controlling the medical device to deliver the neurostimulation therapy comprises controlling the medical device to deliver the neurostimulation therapy during a third quartile of the first fill cycle.

9. The method of claim 1, wherein the one or more physiological markers comprise at least one of a pressure of the bladder, a flow of urine from the bladder, a wetness of an article external of the patient, an electromyogram (EMG) signal, a nerve recording, a posture change, a physical location of the patient within a structure, or a toilet use event.

10. The method of claim 1, further comprising sensing the one or more physiological markers via one or more sensors carried on one or more leads implanted in the patient, wherein the medical device is configured to deliver the neurostimulation therapy via an electrode combination carried on the one or more leads.

11. A system comprising:
    processing circuitry configured to:
    monitor one or more physiological markers associated with fill cycles of a bladder of a patient;
    withhold, based on the monitoring of the one or more physiological markers, neurostimulation therapy delivery to the patient during a first fill cycle;
    control a medical device to deliver the neurostimulation therapy to the patient during the first fill cycle and subsequent to withholding the neurostimulation therapy delivery during the first fill cycle, the neurostimulation therapy configured to inhibit contraction of the bladder of the patient.

12. The system of claim 1, wherein the processing circuitry is configured to withhold the neurostimulation therapy delivery by at least:
    determining, based on monitoring the one or more physiological markers, an end of an initial fill cycle; and
    responsive to determining the end of the initial fill cycle, withholding the neurostimulation therapy delivery during the first fill cycle that immediately follows the initial fill cycle.

13. The system of claim 12, wherein the processing circuitry is configured to determine the end of the initial fill cycle by at least detecting a voiding event of the patient.

14. The system of claim 11, wherein the processing circuitry is configured to:

determine, based on monitoring the one or more physiological markers, an end of the first fill cycle;

responsive to determining the end of the first fill cycle, withhold the neurostimulation therapy delivery during a second fill cycle that immediately follows the first fill cycle; and control the medical device to deliver the neurostimulation therapy to the patient during the second fill cycle and subsequent to withholding the neurostimulation therapy delivery during the second fill cycle.

15. The system of claim 11, wherein the processing circuitry is configured to withhold the neurostimulation therapy delivery by at least withholding delivery of all neurostimulation therapy to the patient.

16. The system of claim 11, wherein the processing circuitry is configured to control the medical device to deliver the neurostimulation therapy by at least determining to deliver the neurostimulation therapy after withholding the neurostimulation therapy by at least:

tracking a time period from a voiding event associated with an initial fill cycle prior to the first fill cycle;

comparing the time period to a fill time threshold; and responsive to the time period exceeding the fill time threshold, controlling the medical device to deliver the neurostimulation therapy during the first fill cycle and subsequent to withholding the neurostimulation therapy during the first fill cycle.

17. The system of claim 16, wherein the processing circuitry is configured to predict the fill time threshold based on respective durations of a plurality of previous fill cycles of the patient.

18. The system of claim 11, wherein the processing circuitry is configured to control the medical device to deliver the neurostimulation therapy by at least controlling the medical device to deliver the neurostimulation therapy during a third quartile of the first fill cycle.

19. The system of claim 11, wherein the one or more physiological markers comprise at least one of a pressure of the bladder, a flow of urine from the bladder, a wetness of an article external of the patient, an electromyogram (EMG) signal, a nerve recording, a posture change, a physical location of the patient within a structure, or a toilet use event.

20. The system of claim 11, further comprising sensing circuitry configured to sense the one or more physiological markers via one or more sensors carried on one or more leads implanted in the patient, wherein the medical device is configured to deliver the neurostimulation therapy via an electrode combination carried on the one or more leads.

21. The system of claim 11, further comprising the medical device, wherein the medical device comprises a therapy delivery module configured to deliver the neurostimulation therapy to the patient.

22. A computer-readable medium comprising instruction that, when executed, cause processing circuitry to:

monitor one or more physiological markers associated with fill cycles of a bladder of a patient;

withhold, based on the monitoring of the one or more physiological markers, neurostimulation therapy delivery to the patient during a first fill cycle;

control a medical device to deliver the neurostimulation therapy to the patient during the first fill cycle and subsequent to withholding the neurostimulation therapy delivery during the first fill cycle, the neurostimulation therapy configured to inhibit contraction of the bladder of the patient.

23. The method of claim 1, further comprising:

receiving, from a sensor associated with the patient, a signal; and determining, based on the signal, the one or more physiological markers indicative of one or more respective phases of a fill cycle of the bladder of the patient.

24. The method of claim 11, wherein the processing circuitry is configured to:

receive, from a sensor associated with the patient, a signal; and determine, based on the signal, the one or more physiological markers indicative of one or more respective phases of a fill cycle of the bladder of the patient.

* * * * *